(12) United States Patent
Evans et al.

(10) Patent No.: US 6,723,531 B2
(45) Date of Patent: *Apr. 20, 2004

(54) METHOD FOR MODULATING EXPRESSION OF EXOGENOUS GENES IN MAMMALIAN SYSTEMS, AND PRODUCTS RELATED THERETO

(75) Inventors: Ronald M. Evans, La Jolla, CA (US); David No, Irvine, CA (US); Enrique Saez, San Diego, CA (US)

(73) Assignee: The Salk Institute for Biological Studies, La Jolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 44 days.

(21) Appl. No.: 09/042,488

(22) Filed: Mar. 16, 1998

(65) Prior Publication Data

US 2002/0177564 A1 Nov. 28, 2002

Related U.S. Application Data

(63) Continuation-in-part of application No. 08/974,530, filed on Nov. 19, 1997, now abandoned, which is a continuation-in-part of application No. 08/628,830, filed on Apr. 5, 1996, now abandoned.

(51) Int. Cl.$^7$ ............... C12P 21/06; C12N 5/00; C12N 15/00; C12N 15/63; A01N 63/00; A01N 43/04; C07H 21/02; C07H 21/04
(52) U.S. Cl. ............... 435/69.1; 435/320.1; 435/325; 435/455; 435/69.7; 424/93.1; 424/93.2; 424/93.21; 514/44; 536/23.1; 536/23.5
(58) Field of Search ............... 514/44; 435/325, 435/320.1, 455, 69.7, 69.1; 424/93.1, 93.2, 93.21; 536/23.1, 23.5

(56) References Cited

U.S. PATENT DOCUMENTS

| | | | |
|---|---|---|---|
| 4,160,452 A | 7/1979 | Theeuwes | 128/260 |
| 4,256,108 A | 3/1981 | Theeuwes | 128/260 |
| 4,265,874 A | 5/1981 | Bonsen et al. | 424/15 |
| 4,394,448 A | 7/1983 | Szoka, Jr. et al. | 435/172 |
| 4,399,216 A | 8/1983 | Axel et al. | 435/6 |
| 4,405,712 A | 9/1983 | Vande Woude et al. | 435/5 |
| 4,619,794 A | 10/1986 | Hauser | 264/4.1 |
| 4,634,665 A | 1/1987 | Axel et al. | 435/68 |
| 4,650,764 A | 3/1987 | Temin et al. | 435/240 |
| 4,870,009 A | 9/1989 | Evans et al. | 435/70 |
| 4,952,496 A | 8/1990 | Studier et al. | 435/91 |
| 4,981,784 A | 1/1991 | Evans et al. | 435/6 |
| 4,985,461 A | 1/1991 | Hsu et al. | 514/615 |
| 5,024,939 A | 6/1991 | Gorman | 435/69.1 |
| 5,071,773 A | 12/1991 | Evans et al. | 436/501 |
| 5,117,057 A | 5/1992 | Hsu et al. | 564/149 |
| 5,171,671 A | 12/1992 | Evans et al. | 435/69.1 |
| 5,198,225 A * | 3/1993 | Meybeck et al. | 424/450 |
| 5,225,443 A | 7/1993 | Murphy et al. | 514/615 |
| 5,252,479 A | 10/1993 | Srivastava | 435/235.1 |
| 5,354,762 A | 10/1994 | Hsu et al. | 514/338 |
| 5,358,967 A | 10/1994 | Carlson | 514/615 |
| 5,399,346 A | 3/1995 | Anderson et al. | 424/93.21 |
| 5,424,333 A | 6/1995 | Wing | 514/615 |
| 5,514,578 A | 5/1996 | Hogness et al. | 435/240.2 |

FOREIGN PATENT DOCUMENTS

| | | | |
|---|---|---|---|
| EP | 0 230 075 A1 | 8/1987 | |
| EP | 0 234 944 A1 | 9/1987 | |
| EP | 0 261 755 A2 | 3/1988 | |
| EP | 0 347 216 A2 | 12/1989 | |
| EP | 0 361 645 A2 | 4/1990 | |
| EP | 0 461 809 A1 | 12/1991 | |
| GB | 2 231 268 A | 11/1990 | |
| WO | WO 89/05345 | 6/1989 | |
| WO | WO 90/06997 | 6/1990 | |
| WO | WO 92/05266 | 4/1992 | |
| WO | WO 92/07573 | 5/1992 | |
| WO | WO 92/14829 | 9/1992 | |
| WO | WO 95/07021 | 3/1995 | |
| WO | WO 95/07615 | 3/1995 | |
| WO | WO 96/37609 | 11/1996 | C12N/15/12 |

OTHER PUBLICATIONS

Kay et al, PNAS 94:12744–12746, 1997.*
Mikitani Biochem. Biophy. Res. Com. 227(2)427–432, 1996.*
Nakagawa wt al Steroids 60(5):401–405, 1995.*
Rosenberg et al., Gene therapist, Heal thyself, 2000, Science, vol. 287, p. 1751.*
Verma, Gene therapy: beyond 2000, 2000, Molecular Therapy, vol. 1, p. 493.*
Friedmann, Principles for human gene therapy studies, 2000, Science, vol. 287, pp. 2163–2164.*
Anderson, Human gene therapy, 1998, Nature, vol. 392, pp. 25–30.*
Verma et al., Gene therapy– promises, problems and prospects, 1997, Nature, vol. 389, pp. 239–242.*
Varmus, Gene therapy: Not ready for primetime, 1996, Nature Medicine, vol. 2, pp. 7–8.*

(List continued on next page.)

*Primary Examiner*—Jeffrey Fredman
*Assistant Examiner*—Sumesh Kaushal
(74) *Attorney, Agent, or Firm*—Stephen E. Reiter; Foley & Lardner

(57) ABSTRACT

In accordance with the present invention, there are provided various methods for modulating the expression of an exogenous gene in a mammalian subject employing modified ecdysone receptors. Also provided are modified ecdysone receptors, as well as homomeric and heterodimeric receptors containing same, nucleic acids encoding invention modified ecdysone receptors, modified ecdysone response elements, gene transfer vectors, recombinant cells, and transgenic animals containing nucleic acids encoding invention modified ecdysone receptor.

25 Claims, 6 Drawing Sheets

OTHER PUBLICATIONS

Hoppe et al., Adenovirus–mediated inducible gene expression in vivo by a hybrid ecdysone receptor, 2000, Molecular Therapy, vol. 1, pp. 159–164.*

Ghbeish et al., The dual role of ultraspiracle, the Drosophilia retinoid X receptor, in the ecdysone response, 2001, PNAS, vol. 98, pp. 3867–3872.*

No et al., Ecdysone–inducible gene expression in mammalian cells and transgenic mice, 1995, Proc. Natl. Acad. Sci. USA, vol. 93, pp. 3346–3351.*

Christopherson et al., Ecdysteroid–dependent regulation of genes in mammalian cells by a Drosophilia ecdysone receptor and chimeric transactivators, 1992, Proc. Natl. Acad. Sci. USA, vol. 89, pp. 6314–6318.*

*Apoptosis, The Molecular Basis of Cell Death*, Current Communications In Cell & Molecular Biology, Cold Spring Harbor Laboratory Press, 1991.

Bosselman et al., "Replication–Defective Chimeric Helper Proviruses and Factors Affecting Generation of Competent Virus: Expression of Moloney Murine Leukemia Virus Structural Genes via the Metallothionein Promoter" *Molecular and Cellular Biology* 7(5):1797–1806 (1987).

Brent and Ptashne, "A Eukaryotic Transcriptional Activator Bearing the DNA Specificity of a Prokaryotic Repressor," *Cell*, 43:729–736 (1985).

Christopherson et al., "Ecdysteroid–dependent regulation of genes in mammalian cells by a Drosophila ecdysone receptor and chimeric transactivators" *Proc. Natl. Acad. Sci.USA*, 89:6314–6318 (1992).

Conaway and Conaway, 1994, "Transcription Mechanisms and Regulation", *Raven Press Series on Molecular and Cellular Biology*, vol. 3, Raven Press, Ltd., New York, NY.

Danos et al., "Safe and efficient generation of recombinant retroviruses with amphotropic and ecotropic host ranges" *Proc. Natl. Acad. Sci. USA* 85:6460–6464 (1988).

Devlin et al., "Random Peptide Libraries: A Source of Specific Protein Binding Molecules" *Science*, 249:404–406 (1990).

Evans R.M., "The Steroid and Thyroid Hormone Receptor Superfamily" *Science* 240:889–895 (1988).

Forman et al., "Identification of a Nuclear Receptor That Is Activated by Farnesol Metabolites" *Cell* 81:687–693 (1995).

Freedman et al., "The function and structure of the metal coordination sites within the glucocorticoid receptor DNA binding domain" *Nature* 334:543–546 (1988).

Friedmann, T., "Progress Toward Human Gene Therapy" *Science* 244:1275–1281 (1989).

Furth et al., "Temporal control of gene expression in transgenic mice by a tetracylcline–responsive promoter" *Proc. Natl. Acad. Sci. USA* 91: 9302–9306 (1994).

Giguere et al., "Identification of a receptor for the morphogen retinoic acid" *Nature* 330:624–629 (1987).

Glass et al., "The Thyroid Hormone Receptor Binds with Opposite Transcriptional Effects to a Common Sequence Motif in Thyroid Hormone and Estrogen Responses Elements" *Cell* 54:313–323 (1988).

Gossen et al., "Control of gene activity in higher eukaryotic cells by prokaryotic regulatory elements" *TIBS* 18:471–475 (1993).

Gossen et al., "Tight Control of gene expression in mammalian cells by tetracycline–responsive promoters" *Proc. Natl. Acad. Sci.* 89:5547–5551 (1992).

Gossen et al., "Transcriptional Activation by Tetracyclines in Mammalian Cells" *Science* 268:1766–1769 (1995).

Green and Chambon, "Nuclear receptor enhance our understanding of transcription regulation" *Trends Genet.* 4:309–314 (1988).

Green and Chambon, "Oestradiol induction of a glucocortiocoid–responsive gene by a chimaeric receptor" *Nature* 325:75–78 (1987).

Harrison, "A structural taxonomy of DNA–binding domains" *Nature* 353:715–719.

Hollenberg and Evans, "Multiple and Cooperative Trans–Activation Domains of the Human Glucocorticoid Receptor" *Cell* 55:899–906 (1988).

Jacobs and Michaels, "Zinc Finger Gene Database" *The New Biologist* 2(6):583 (1990).

Jacobs, G.H., "Determination of the base recognition positions of zinc fingers from sequence analysis" *The EMBO Journal* 11:4507–4517 (1992).

Jaenisch, R., "Transgenic Animals" *Science* 240:1468–1474 (1988).

Kamine et al., "Sp1–dependent activation of a synthetic promoter by human immunodeficiency virus type 1 Tat protein" *Proc. Natl. Acad. Sci. USA* 88:8510–8514 (1991).

Klock et al., "Oestrogen and glucocorticoid responsive elements are closely related but distinct" *Nature* 329:734–736 (1987).

Klug and Rhodes, 'Zince fingers': a novel protein motif for nucleic acid recognition *TIBS* 12:464–469 (1987).

Koelle et al., "The Drosophila EcR Gene Encodes an Ecdysone Receptor, a New Member of the Steroid Receptor Superfamily" *Cell* 67:59–77 (1991).

Kumar and Chambon, "The Estrogen Receptor Binds Tightly to Its Responsive Element as a Ligand–Induced Homodimer" *Cell* 55:145–156 (1988).

Kumar et al., "Functional Domains of the Human Estrogen Receptor" *Cell* 51:941–951 (1987).

Ladias et al., "Regulation of the Apolipoprotein AI Gene by ARP–1, a Novel Member of the Steroid Receptor Superfamily" *Science* 251:561–565 (1991).

Lee et al., CD8 Surface Levels Alter the Fate of $\alpha/\beta$ T Cell Receptor–expressing Thymocytes in Transgenic Mice *J. Exp. Med.* 175:1013–1025 (1992).

Leonard et al., "Characterization of Somatostatin Transactivating Factor–1, a Novel Homeobox Factor That Stimulates Somatostatin Expression in Pancreatic Islet Cells" *Molecular Endocrinology* 7(10):1275–1283.

Mangelsdorf et al., "The Retinoid Receptors" *The Retinoids: Biology, Chemistry, and Medicine, 2nd Edition* 8:319–349 (1994).

Markowitz, et al. "A Safe Packaging Line for Gene Transfer: Separating Viral Genes on Two Different Plasmids" *Journal of Virology* 61(4):1120–1124 (1988).

Miller et al., "Repetitive zinc–binding domains in the protein transcription factor IIIA from Xenopus oocytes" *The EMBO Journal* 4(6):1609–1614 (1985).

Miller, A. D., "Retrovirus Packaging Cells" *Human Gene Therapy* 1:5–14 (1990).

Miyajima et al., "Identification of two novel members of erbA superfamily by molecular cloning: the gene products of the two are highly related to each other" *Nucleic Acids Research* 16(23): 11057–11074 (1988).

Mlodzik et al., "The Drosophila seven–up Gene, a Member of the Steroid Receptor Gene Superfamily, Controls Photoreceptor Cell Fates" *Cell* 60:211–224 (1990).

Mulligan et al., "Synthesis of rabbit β–globin in cultured monkey kidney cells following infection with a SV40 β–globin recombinant genome" *Nature* 277:108–114 (1977).

Mulligan, R. C., "The Basic Science of Gene Therapy" *Science* 260:926–932 (1993).

Nakamura et al., "DNA Sequence of the Gene for the Outer Membrance Lipoprotein of *E. coli*: an Extremely AT–Rich Promoter" *Cell*, 18:1109–1117 (1979).

O'Gorman et al., "Recombinase–Mediated Gene Activation and Site–Specific Integration in Mammalian Cells" *Science* 251:1351–1355 (1991).

Perlmann et al., "Determinants for selective RAR and TR recognition of direct repeat HREs" *Genes & Devel.* 7:1411–1422 (1993).

Petkovich et al., "A human retinoic acid receptor which belongs to the family of nuclear receptors" *Nature* 330:444–450 (1987).

Ross et al. "Targeted expression of a toxin gene to adipose tissue: transgenic mice resistant to obesity" *Genes and Development* 7:1318–1324 (1983).

Scott and Smith, "Searching for Peptide Ligands with an Epitope Library" *Science* 249:386–390 (1990).

Scott et al., "The structure and function of the Homoeodomain" *Biochimica et Biophysica Acta* 989:25–48 (1989).

Severne et al., "Metal binding 'finger' structures in the glucocorticoid receptor defined by site–directed mutagenesis" *EMBO J.* 7(8):2503–2508 (1988).

Shackleford et al., "Construction of a clonable, infectious, and tumorigenic mouse mammary tumor virus provirus and a derivative genetic vector" *Proc. Natl. Acad. Sci. USA* 85:9655–9659 (1988).

Shockett et al., "A modified tetracycline–regulated system provides autoregulatory, inducible gene expression in cultured cells and transgenic mice" *Proc. Natl. Acad. Sci.* 92:6522–6526 (1995).

Sladek et al., "Liver–enriched transcription factor HNF–4 is a novel member of the steroid hormone receptor superfamily" *Genes & Development* 4:2353–2365 (1990).

Strähle et al., "Synergistic action of the glucocortiocoid receptor with transcription factors" *EMBO* 7(11):3389–3395 (1988).

Studier et al., "[6] Use of T7 RNA Polymerase to Direct Expression of Cloned Genes" *Methods in Enzymology* 185:60–89 (1990).

Thompson and Evans, "Trans–activation by thyroid hormone receptors: Functional parallels with steroid hormone receptors" *Proc. Natl. Acad. Sci. U.S.A.* 86:3494–3498 (1989).

Umesono and Evans, "Determinants of Target Gene Specificity for Steroid/Thyroid Hormone Receptors" *Cell* 57:1139–1146 (1989).

Umesono et al., "Retinoic acid and thyroid hormone induce gene expression through a common responsive element" *Nature* 336:262–265 (1988).

Underhill et al., "Constitutively Active Retinoid Receptors Exhibit Interfamily and Intrafamily Promoter Specificity" *Molecular Endocrinology* 8:274–285 (1994).

Urlaub et al., "Effect of Gamma Rays at the Dihydrofolate Reductase Locus: Deletions and Inversion" *Somatic Cell and Molecular Genetics* 12(6):555–566 (1986).

Wang et al., "COUP transcription factor is a member of the steroid receptor superfamily" *Nature* 340:163–166 (1989).

Watanabe et al., "Construction of a Helper Cell Line for Avian Reticuloendotheliosis Virus Cloning Vectors" *Molecular and Cellular Biology* 3(12):2241–2249 (1983).

Wong, et al., "Human GM–CSF: Molecular Cloning of the Complementary DNA and Purification of the Natural and Recombinant Proteins" *Science* 228:810–815 (1985).

Yamamoto, K.R., "Steroid Receptor Regulated Transcription of Specific Genes and Gene Networks" *Ann. Rev. Genet.* 19:209–252 (1985).

Yao et al., "Drosophila ultraspiracle Modulates Ecdysone Receptor Function via Heterodimer Formation" *Cell* 71:63–72 (1992).

Yao et al., "Functional ecdysone receptor is the product of EcR and *Ultraspriacle* genes" *Nature* 366:476–479 (1933).

* cited by examiner

SEQUENCE LISTING

<160> NUMBER OF SEQ ID NOS: 18

<210> SEQ ID NO 1
<211> LENGTH: 71
<212> TYPE: PRT
<213> ORGANISM: Artificial Sequence
<220> FEATURE:
<223> OTHER INFORMATION: Description of Artificial Sequence: Consensus
      peptide sequence
<221> NAME/KEY: MOD_RES
<222> LOCATION: (2)..(3)
<223> OTHER INFORMATION: Any amino acid
<221> NAME/KEY: MOD_RES
<222> LOCATION: (5)..(6)
<223> OTHER INFORMATION: Any amino acid
<221> NAME/KEY: MOD_RES
<222> LOCATION: (8)
<223> OTHER INFORMATION: Any amino acid
<221> NAME/KEY: MOD_RES
<222> LOCATION: (10)
<223> OTHER INFORMATION: Any amino acid
<221> NAME/KEY: MOD_RES
<222> LOCATION: (12)
<223> OTHER INFORMATION: Any amino acid
<221> NAME/KEY: MOD_RES
<222> LOCATION: (14)..(17)
<223> OTHER INFORMATION: Any amino acid
<221> NAME/KEY: MOD_RES

```
<222> LOCATION: (19)..(20)
<223> OTHER INFORMATION: Any amino acid
<221> NAME/KEY: MOD_RES
<222> LOCATION: (23)
<223> OTHER INFORMATION: Any amino acid
<221> NAME/KEY: MOD_RES
<222> LOCATION: (26)
<223> OTHER INFORMATION: Any amino acid
<221> NAME/KEY: MOD_RES
<222> LOCATION: (28)..(38)
<223> OTHER INFORMATION: Any amino acid
<221> NAME/KEY: MOD_RES
<222> LOCATION: (40)..(47)
<223> OTHER INFORMATION: Any amino acid
<221> NAME/KEY: MOD_RES
<222> LOCATION: (49)..(51)
<223> OTHER INFORMATION: Any amino acid
<221> NAME/KEY: MOD_RES
<222> LOCATION: (53)..(54)
<223> OTHER INFORMATION: Any amino acid
<221> NAME/KEY: MOD_RES
<222> LOCATION: (56)..(57)
<223> OTHER INFORMATION: Any amino acid
<221> NAME/KEY: MOD_RES
<222> LOCATION: (59)..(60)
<223> OTHER INFORMATION: Any amino acid
<221> NAME/KEY: MOD_RES
<222> LOCATION: (63)..(64)
<223> OTHER INFORMATION: Any amino acid
<221> NAME/KEY: MOD_RES
<222> LOCATION: (67)..(69)
<223> OTHER INFORMATION: Any amino acid

<400> SEQUENCE: 1

Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
 65                  70

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Gly Cys Lys Gly
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ser Cys Lys Val
 1               5
```

```
<210> SEQ ID NO 4
<211> LENGTH: 2241
<212> TYPE: DNA
<213> ORGANISM: Artificial Sequence
<220> FEATURE:
<223> OTHER INFORMATION: Description of Artificial Sequence: Recombinant
      VgEcR
<221> NAME/KEY: CDS
<222> LOCATION: (1)..(2238)

<400> SEQUENCE: 4 atg gcc ccc ccg acc gat gtc agc ctg ggg gac gag ctc cac tta gac        48
Met Ala Pro Pro Thr Asp Val Ser Leu Gly Asp Glu Leu His Leu Asp
 1               5                  10                  15 ggc gag gac gtg gcg atg gcg cat gcc gac gcg cta gac gat ttc gat        96
Gly Glu Asp Val Ala Met Ala His Ala Asp Ala Leu Asp Asp Phe Asp
             20                  25                  30 ctg gac atg ttg ggg gac ggg gat tcc ccg ggt ccg gga ttt acc ccc       144
Leu Asp Met Leu Gly Asp Gly Asp Ser Pro Gly Pro Gly Phe Thr Pro
         35                  40                  45 cac gac tcc gcc ccc tac ggc gct ctg gat atg gcc gac ttc gag ttt       192
His Asp Ser Ala Pro Tyr Gly Ala Leu Asp Met Ala Asp Phe Glu Phe
     50                  55                  60 gag cag atg ttt acc gat gcc ctt gga att gac gag tac ggt ggg aag       240
Glu Gln Met Phe Thr Asp Ala Leu Gly Ile Asp Glu Tyr Gly Gly Lys
 65                  70                  75                  80 ctt cta ggt acc tct aga agg ata tcg aat tct ata tct tca ggt cgc       288
Leu Leu Gly Thr Ser Arg Arg Ile Ser Asn Ser Ile Ser Ser Gly Arg
                 85                  90                  95 gat gat ctc tcg cct tcg agc agc ttg aac gga tac tcg gcg aac gaa       336
Asp Asp Leu Ser Pro Ser Ser Ser Leu Asn Gly Tyr Ser Ala Asn Glu
            100                 105                 110 agc tgc gat gcg aag aag agc aag aag gga cct gcg cca cgg gtg caa       384
Ser Cys Asp Ala Lys Lys Ser Lys Lys Gly Pro Ala Pro Arg Val Gln
        115                 120                 125 gag gag ctg tgc ctg gtt tgc ggc gac agg gcc tcc ggc tac cac tac       432
Glu Glu Leu Cys Leu Val Cys Gly Asp Arg Ala Ser Gly Tyr His Tyr
    130                 135                 140 aac gcc ctc acc tgt gga tcc tgc aag gtg ttc ttt cga cgc agc gtt       480
Asn Ala Leu Thr Cys Gly Ser Cys Lys Val Phe Phe Arg Arg Ser Val
145                 150                 155                 160 acg aag agc gcc gtc tac tgc tgc aag ttc ggg cgc gcc tgc gaa atg       528
Thr Lys Ser Ala Val Tyr Cys Cys Lys Phe Gly Arg Ala Cys Glu Met
                165                 170                 175 gac atg tac atg agg cga aag tgt cag gag tgc cgc ctg aaa aag tgc       576
Asp Met Tyr Met Arg Arg Lys Cys Gln Glu Cys Arg Leu Lys Lys Cys
            180                 185                 190 ctg gcc gtg ggt atg cgg ccg gaa tgc gtc gtc ccg gag aac caa tgt       624
Leu Ala Val Gly Met Arg Pro Glu Cys Val Val Pro Glu Asn Gln Cys
        195                 200                 205 gcg atg aag cgg cgc gaa aag aag gcc cag aag gag aag gac aaa atg       672
Ala Met Lys Arg Arg Glu Lys Lys Ala Gln Lys Glu Lys Asp Lys Met
    210                 215                 220 acc act tcg ccg agc tct cag cat ggc ggc aat ggc agc ttg gcc tct       720
Thr Thr Ser Pro Ser Ser Gln His Gly Gly Asn Gly Ser Leu Ala Ser
225                 230                 235                 240 ggt ggc ggc caa gac ttt gtt aag aag gag att ctt gac ctt atg aca       768
Gly Gly Gly Gln Asp Phe Val Lys Lys Glu Ile Leu Asp Leu Met Thr
                245                 250                 255 tgc gag ccg ccc cag cat gcc act att ccg cta cta cct gat gaa ata       816
Cys Glu Pro Pro Gln His Ala Thr Ile Pro Leu Leu Pro Asp Glu Ile
            260                 265                 270
```

```
ttg gcc aag tgt caa gcg cgc aat ata cct tcc tta acg tac aat cag      864
Leu Ala Lys Cys Gln Ala Arg Asn Ile Pro Ser Leu Thr Tyr Asn Gln
        275                 280                 285 ttg gcc gtt ata tac aag tta att tgg tac cag gat ggc tat gag cag      912
Leu Ala Val Ile Tyr Lys Leu Ile Trp Tyr Gln Asp Gly Tyr Glu Gln
        290                 295                 300 cca tct gaa gag gat ctc agg cgt ata atg agt caa ccc gat gag aac      960
Pro Ser Glu Glu Asp Leu Arg Arg Ile Met Ser Gln Pro Asp Glu Asn
305                 310                 315                 320 gag agc caa acg gac gtc agc ttt cgg cat ata acc gag ata acc ata     1008
Glu Ser Gln Thr Asp Val Ser Phe Arg His Ile Thr Glu Ile Thr Ile
                325                 330                 335 ctc acg gtc cag ttg att gtt gag ttt gct aaa ggt cta cca gcg ttt     1056
Leu Thr Val Gln Leu Ile Val Glu Phe Ala Lys Gly Leu Pro Ala Phe
        340                 345                 350 aca aag ata ccc cag gag gac cag atc acg tta cta aag gcc tgc tcg     1104
Thr Lys Ile Pro Gln Glu Asp Gln Ile Thr Leu Leu Lys Ala Cys Ser
        355                 360                 365 tcg gag gtg atg atg ctg cgt atg gca cga cgc tat gac cac agc tcg     1152
Ser Glu Val Met Met Leu Arg Met Ala Arg Arg Tyr Asp His Ser Ser
        370                 375                 380 gac tca ata ttc ttc gcg aat aat aga tca tat acg cgg gat tct tac     1200
Asp Ser Ile Phe Phe Ala Asn Asn Arg Ser Tyr Thr Arg Asp Ser Tyr
385                 390                 395                 400 aaa atg gcc gga atg gct gat aac att gaa gac ctg ctg cat ttc tgc     1248
Lys Met Ala Gly Met Ala Asp Asn Ile Glu Asp Leu Leu His Phe Cys
                405                 410                 415 cgc caa atg ttc tcg atg aag gtg gac aac gtc gaa tac gcg ctt ctc     1296
Arg Gln Met Phe Ser Met Lys Val Asp Asn Val Glu Tyr Ala Leu Leu
        420                 425                 430 act gcc att gtg atc ttc tcg gac cgg ccg ggc ctg gag aag gcc caa     1344
Thr Ala Ile Val Ile Phe Ser Asp Arg Pro Gly Leu Glu Lys Ala Gln
        435                 440                 445 cta gtc gaa gcg atc cag agc tac tac atc gac acg cta cgc att tat     1392
Leu Val Glu Ala Ile Gln Ser Tyr Tyr Ile Asp Thr Leu Arg Ile Tyr
450                 455                 460 ata ctc aac cgc cac tgc ggc gac tca atg agc ctc gtc ttc tac gca     1440
Ile Leu Asn Arg His Cys Gly Asp Ser Met Ser Leu Val Phe Tyr Ala
465                 470                 475                 480 aag ctg ctc tcg atc ctc acc gag ctg cgt acg ctg ggc aac cag aac     1488
Lys Leu Leu Ser Ile Leu Thr Glu Leu Arg Thr Leu Gly Asn Gln Asn
                485                 490                 495 gcc gag atg tgt ttc tca cta aag ctc aaa aac cgc aaa ctg ccc aag     1536
Ala Glu Met Cys Phe Ser Leu Lys Leu Lys Asn Arg Lys Leu Pro Lys
        500                 505                 510 ttc ctc gag gag atc tgg gac gtt cat gcc atc ccg cca tcg gtc cag     1584
Phe Leu Glu Glu Ile Trp Asp Val His Ala Ile Pro Pro Ser Val Gln
        515                 520                 525 tcg cac ctt cag att acc cag gag gag aac gag cgt ctc gag cgg gct     1632
Ser His Leu Gln Ile Thr Gln Glu Glu Asn Glu Arg Leu Glu Arg Ala
        530                 535                 540 gag cgt atg cgg gca tcg gtt ggg ggc gcc att acc gcc ggc att gat     1680
Glu Arg Met Arg Ala Ser Val Gly Gly Ala Ile Thr Ala Gly Ile Asp
545                 550                 555                 560 tgc gac tct gcc tcc act tcg gcg gcg gca gcc gcg gcc cag cat cag     1728
Cys Asp Ser Ala Ser Thr Ser Ala Ala Ala Ala Ala Ala Gln His Gln
                565                 570                 575 cct cag cct cag ccc cag ccc caa ccc tcc tcc ctg acc cag aac gat     1776
Pro Gln Pro Gln Pro Gln Pro Gln Pro Ser Ser Leu Thr Gln Asn Asp
```

-continued

```
                       580                 585                 590
tcc cag cac cag aca cag ccg cag cta caa cct cag cta cca cct cag      1824
Ser Gln His Gln Thr Gln Pro Gln Leu Gln Pro Gln Leu Pro Pro Gln
            595                 600                 605 ctg caa ggt caa ctg caa ccc cag ctc caa cca cag ctt cag acg caa      1872
Leu Gln Gly Gln Leu Gln Pro Gln Leu Gln Pro Gln Leu Gln Thr Gln
    610                 615                 620 ctc cag cca cag att caa cca cag cca cag ctc ctt ccc gtc tcc gct      1920
Leu Gln Pro Gln Ile Gln Pro Gln Pro Gln Leu Leu Pro Val Ser Ala
625                 630                 635                 640 ccc gtg ccc gcc tcc gta acc gca cct ggt tcc ttg tcc gcg gtc agt      1968
Pro Val Pro Ala Ser Val Thr Ala Pro Gly Ser Leu Ser Ala Val Ser
                645                 650                 655 acg agc agc gaa tac atg ggc gga agt gcg gcc ata gga ccc atc acg      2016
Thr Ser Ser Glu Tyr Met Gly Gly Ser Ala Ala Ile Gly Pro Ile Thr
            660                 665                 670 ccg gca acc acc agc agt atc acg gct gcc gtt acc gct agc tcc acc      2064
Pro Ala Thr Thr Ser Ser Ile Thr Ala Ala Val Thr Ala Ser Ser Thr
    675                 680                 685 aca tca gcg gta ccg atg ggc aac gga gtt gga gtc ggt gtt ggg gtg      2112
Thr Ser Ala Val Pro Met Gly Asn Gly Val Gly Val Gly Val Gly Val
690                 695                 700 ggc ggc aac gtc agc atg tat gcg aac gcc cag acg gcg atg gcc ttg      2160
Gly Gly Asn Val Ser Met Tyr Ala Asn Ala Gln Thr Ala Met Ala Leu
705                 710                 715                 720 atg ggt gta gcc ctg cat tcg cac caa gag cag ctt atc ggg gga gtg      2208
Met Gly Val Ala Leu His Ser His Gln Glu Gln Leu Ile Gly Gly Val
                725                 730                 735 gcg gtt aag tcg gag cac tcg acg act gca tag                         2241
Ala Val Lys Ser Glu His Ser Thr Thr Ala
            740                 745

<210> SEQ ID NO 5
<211> LENGTH: 746
<212> TYPE: PRT
<213> ORGANISM: Artificial Sequence
<220> FEATURE:
<223> OTHER INFORMATION: Description of Artificial Sequence: Recombinant
      VgEcR

<400> SEQUENCE: 5

Met Ala Pro Pro Thr Asp Val Ser Leu Gly Asp Glu Leu His Leu Asp
 1               5                  10                  15

Gly Glu Asp Val Ala Met Ala His Ala Asp Ala Leu Asp Asp Phe Asp
            20                  25                  30

Leu Asp Met Leu Gly Asp Gly Asp Ser Pro Gly Pro Gly Phe Thr Pro
        35                  40                  45

His Asp Ser Ala Pro Tyr Gly Ala Leu Asp Met Ala Asp Phe Glu Phe
    50                  55                  60

Glu Gln Met Phe Thr Asp Ala Leu Gly Ile Asp Glu Tyr Gly Gly Lys
65                  70                  75                  80

Leu Leu Gly Thr Ser Arg Arg Ile Ser Asn Ser Ile Ser Ser Gly Arg
                85                  90                  95

Asp Asp Leu Ser Pro Ser Ser Leu Asn Gly Tyr Ser Ala Asn Glu
            100                 105                 110

Ser Cys Asp Ala Lys Lys Ser Lys Lys Gly Pro Ala Pro Arg Val Gln
        115                 120                 125

Glu Glu Leu Cys Leu Val Cys Gly Asp Arg Ala Ser Gly Tyr His Tyr
    130                 135                 140
```

-continued

```
Asn Ala Leu Thr Cys Gly Ser Cys Lys Val Phe Phe Arg Arg Ser Val
145                 150                 155                 160

Thr Lys Ser Ala Val Tyr Cys Cys Lys Phe Gly Arg Ala Cys Glu Met
            165                 170                 175

Asp Met Tyr Met Arg Arg Lys Cys Gln Glu Cys Arg Leu Lys Lys Cys
            180                 185                 190

Leu Ala Val Gly Met Arg Pro Glu Cys Val Val Pro Glu Asn Gln Cys
            195                 200                 205

Ala Met Lys Arg Arg Glu Lys Lys Ala Gln Lys Glu Lys Asp Lys Met
        210                 215                 220

Thr Thr Ser Pro Ser Ser Gln His Gly Gly Asn Gly Ser Leu Ala Ser
225                 230                 235                 240

Gly Gly Gly Gln Asp Phe Val Lys Lys Glu Ile Leu Asp Leu Met Thr
                245                 250                 255

Cys Glu Pro Pro Gln His Ala Thr Ile Pro Leu Leu Pro Asp Glu Ile
            260                 265                 270

Leu Ala Lys Cys Gln Ala Arg Asn Ile Pro Ser Leu Thr Tyr Asn Gln
        275                 280                 285

Leu Ala Val Ile Tyr Lys Leu Ile Trp Tyr Gln Asp Gly Tyr Glu Gln
        290                 295                 300

Pro Ser Glu Glu Asp Leu Arg Arg Ile Met Ser Gln Pro Asp Glu Asn
305                 310                 315                 320

Glu Ser Gln Thr Asp Val Ser Phe Arg His Ile Thr Glu Ile Thr Ile
                325                 330                 335

Leu Thr Val Gln Leu Ile Val Glu Phe Ala Lys Gly Leu Pro Ala Phe
            340                 345                 350

Thr Lys Ile Pro Gln Glu Asp Gln Ile Thr Leu Leu Lys Ala Cys Ser
            355                 360                 365

Ser Glu Val Met Met Leu Arg Met Ala Arg Arg Tyr Asp His Ser Ser
        370                 375                 380

Asp Ser Ile Phe Phe Ala Asn Asn Arg Ser Tyr Thr Arg Asp Ser Tyr
385                 390                 395                 400

Lys Met Ala Gly Met Ala Asp Asn Ile Glu Asp Leu Leu His Phe Cys
                405                 410                 415

Arg Gln Met Phe Ser Met Lys Val Asp Asn Val Glu Tyr Ala Leu Leu
            420                 425                 430

Thr Ala Ile Val Ile Phe Ser Asp Arg Pro Gly Leu Glu Lys Ala Gln
            435                 440                 445

Leu Val Glu Ala Ile Gln Ser Tyr Tyr Ile Asp Thr Leu Arg Ile Tyr
450                 455                 460

Ile Leu Asn Arg His Cys Gly Asp Ser Met Ser Leu Val Phe Tyr Ala
465                 470                 475                 480

Lys Leu Leu Ser Ile Leu Thr Glu Leu Arg Thr Leu Gly Asn Gln Asn
                485                 490                 495

Ala Glu Met Cys Phe Ser Leu Lys Leu Lys Asn Arg Lys Leu Pro Lys
            500                 505                 510

Phe Leu Glu Glu Ile Trp Asp Val His Ala Ile Pro Pro Ser Val Gln
            515                 520                 525

Ser His Leu Gln Ile Thr Gln Glu Glu Asn Glu Arg Leu Glu Arg Ala
        530                 535                 540

Glu Arg Met Arg Ala Ser Val Gly Gly Ala Ile Thr Ala Gly Ile Asp
545                 550                 555                 560
```

```
Cys Asp Ser Ala Ser Thr Ser Ala Ala Ala Ala Gln His Gln
            565                 570                 575

Pro Gln Pro Gln Pro Gln Pro Ser Ser Leu Thr Gln Asn Asp
            580                 585                 590

Ser Gln His Gln Thr Gln Pro Gln Leu Gln Pro Gln Leu Pro Pro Gln
            595                 600                 605

Leu Gln Gly Gln Leu Gln Pro Gln Leu Gln Pro Gln Leu Gln Thr Gln
    610                 615                 620

Leu Gln Pro Gln Ile Gln Pro Gln Pro Gln Leu Leu Pro Val Ser Ala
625                 630                 635                 640

Pro Val Pro Ala Ser Val Thr Ala Pro Gly Ser Leu Ser Ala Val Ser
            645                 650                 655

Thr Ser Ser Glu Tyr Met Gly Gly Ser Ala Ala Ile Gly Pro Ile Thr
            660                 665                 670

Pro Ala Thr Thr Ser Ser Ile Thr Ala Ala Val Thr Ala Ser Ser Thr
            675                 680                 685

Thr Ser Ala Val Pro Met Gly Asn Gly Val Gly Val Gly Val Gly Val
            690                 695                 700

Gly Gly Asn Val Ser Met Tyr Ala Asn Ala Gln Thr Ala Met Ala Leu
705                 710                 715                 720

Met Gly Val Ala Leu His Ser His Gln Glu Gln Leu Ile Gly Gly Val
            725                 730                 735

Ala Val Lys Ser Glu His Ser Thr Thr Ala
            740                 745
```

```
<210> SEQ ID NO 6
<211> LENGTH: 2241
<212> TYPE: DNA
<213> ORGANISM: Artificial Sequence
<220> FEATURE:
<223> OTHER INFORMATION: Description of Artificial Sequence: Recombinant
      VpEcR
<221> NAME/KEY: CDS
<222> LOCATION: (1)..(2238)

<400> SEQUENCE: 6 atg gcc ccc ccg acc gat gtc agc ctg ggg gac gag ctc cac tta gac     48
Met Ala Pro Pro Thr Asp Val Ser Leu Gly Asp Glu Leu His Leu Asp
1               5                   10                  15 ggc gag gac gtg gcg atg gcg cat gcc gac gcg cta gac gat ttc gat     96
Gly Glu Asp Val Ala Met Ala His Ala Asp Ala Leu Asp Asp Phe Asp
                20                  25                  30 ctg gac atg ttg ggg gac ggg gat tcc ccg ggt ccg gga ttt acc ccc    144
Leu Asp Met Leu Gly Asp Gly Asp Ser Pro Gly Pro Gly Phe Thr Pro
            35                  40                  45 cac gac tcc gcc ccc tac ggc gct ctg gat atg gcc gac ttc gag ttt    192
His Asp Ser Ala Pro Tyr Gly Ala Leu Asp Met Ala Asp Phe Glu Phe
        50                  55                  60 gag cag atg ttt acc gat gcc ctt gga att gac gag tac ggt ggg aag    240
Glu Gln Met Phe Thr Asp Ala Leu Gly Ile Asp Glu Tyr Gly Gly Lys
65                  70                  75                  80 ctt cta ggt acc tct aga agg ata tcg aat tct ata tct tca ggt cgc    288
Leu Leu Gly Thr Ser Arg Arg Ile Ser Asn Ser Ile Ser Ser Gly Arg
                85                  90                  95 gat gat ctc tcg cct tcg agc agc ttg aac gga tac tcg gcg aac gaa    336
Asp Asp Leu Ser Pro Ser Ser Ser Leu Asn Gly Tyr Ser Ala Asn Glu
            100                 105                 110 agc tgc gat gcg aag aag agc aag aag gga cct gcg cca cgg gtg caa    384
Ser Cys Asp Ala Lys Lys Ser Lys Lys Gly Pro Ala Pro Arg Val Gln
```

-continued

```
                  115                 120                      125
gag gag ctg tgc ctg gtt tgc ggc gac agg gcc tcc ggc tac cac tac       432
Glu Glu Leu Cys Leu Val Cys Gly Asp Arg Ala Ser Gly Tyr His Tyr
        130                 135                 140 aac gcc ctc acc tgt gag ggc tgc aag ggg ttc ttt cga cgc agc gtt       480
Asn Ala Leu Thr Cys Glu Gly Cys Lys Gly Phe Phe Arg Arg Ser Val
145                 150                 155                 160 acg aag agc gcc gtc tac tgc tgc aag ttc ggg cgc gcc tgc gaa atg       528
Thr Lys Ser Ala Val Tyr Cys Cys Lys Phe Gly Arg Ala Cys Glu Met
                165                 170                 175 gac atg tac atg agg cga aag tgt cag gag tgc cgc ctg aaa aag tgc       576
Asp Met Tyr Met Arg Arg Lys Cys Gln Glu Cys Arg Leu Lys Lys Cys
            180                 185                 190 ctg gcc gtg ggt atg cgg ccg gaa tgc gtc gtc ccg gag aac caa tgt       624
Leu Ala Val Gly Met Arg Pro Glu Cys Val Val Pro Glu Asn Gln Cys
        195                 200                 205 gcg atg aag cgg cgc gaa aag aag gcc cag aag gag aag gac aaa atg       672
Ala Met Lys Arg Arg Glu Lys Lys Ala Gln Lys Glu Lys Asp Lys Met
    210                 215                 220 acc act tcg ccg agc tct cag cat ggc ggc aat ggc agc ttg gcc tct       720
Thr Thr Ser Pro Ser Ser Gln His Gly Gly Asn Gly Ser Leu Ala Ser
225                 230                 235                 240 ggt ggc ggc caa gac ttt gtt aag aag gag att ctt gac ctt atg aca       768
Gly Gly Gly Gln Asp Phe Val Lys Lys Glu Ile Leu Asp Leu Met Thr
                245                 250                 255 tgc gag ccg ccc cag cat gcc act att ccg cta cta cct gat gaa ata       816
Cys Glu Pro Pro Gln His Ala Thr Ile Pro Leu Leu Pro Asp Glu Ile
            260                 265                 270 ttg gcc aag tgt caa gcg cgc aat ata cct tcc tta acg tac aat cag       864
Leu Ala Lys Cys Gln Ala Arg Asn Ile Pro Ser Leu Thr Tyr Asn Gln
        275                 280                 285 ttg gcc gtt ata tac aag tta att tgg tac cag gat ggc tat gag cag       912
Leu Ala Val Ile Tyr Lys Leu Ile Trp Tyr Gln Asp Gly Tyr Glu Gln
    290                 295                 300 cca tct gaa gag gat ctc agg cgt ata atg agt caa ccc gat gag aac       960
Pro Ser Glu Glu Asp Leu Arg Arg Ile Met Ser Gln Pro Asp Glu Asn
305                 310                 315                 320 gag agc caa acg gac gtc agc ttt cgg cat ata acc gag ata acc ata      1008
Glu Ser Gln Thr Asp Val Ser Phe Arg His Ile Thr Glu Ile Thr Ile
                325                 330                 335 ctc acg gtc cag ttg att gtt gag ttt gct aaa ggt cta cca gcg ttt      1056
Leu Thr Val Gln Leu Ile Val Glu Phe Ala Lys Gly Leu Pro Ala Phe
            340                 345                 350 aca aag ata ccc cag gag gac cag atc acg tta cta aag gcc tgc tcg      1104
Thr Lys Ile Pro Gln Glu Asp Gln Ile Thr Leu Leu Lys Ala Cys Ser
        355                 360                 365 tcg gag gtg atg atg ctg cgt atg gca cga cgc tat gac cac agc tcg      1152
Ser Glu Val Met Met Leu Arg Met Ala Arg Arg Tyr Asp His Ser Ser
    370                 375                 380 gac tca ata ttc ttc gcg aat aat aga tca tat acg cgg gat tct tac      1200
Asp Ser Ile Phe Phe Ala Asn Asn Arg Ser Tyr Thr Arg Asp Ser Tyr
385                 390                 395                 400 aaa atg gcc gga atg gct gat aac att gaa gac ctg ctg cat ttc tgc      1248
Lys Met Ala Gly Met Ala Asp Asn Ile Glu Asp Leu Leu His Phe Cys
                405                 410                 415 cgc caa atg ttc tcg atg aag gtg gac aac gtc gaa tac gcg ctt ctc      1296
Arg Gln Met Phe Ser Met Lys Val Asp Asn Val Glu Tyr Ala Leu Leu
            420                 425                 430 act gcc att gtg atc ttc tcg gac cgg ccg ggc ctg gag aag gcc caa      1344
```

```
                                                                          -continued Thr Ala Ile Val Ile Phe Ser Asp Arg Pro Gly Leu Glu Lys Ala Gln
        435                 440                 445 cta gtc gaa gcg atc cag agc tac tac atc gac acg cta cgc att tat      1392
Leu Val Glu Ala Ile Gln Ser Tyr Tyr Ile Asp Thr Leu Arg Ile Tyr
        450                 455                 460 ata ctc aac cgc cac tgc ggc gac tca atg agc ctc gtc ttc tac gca      1440
Ile Leu Asn Arg His Cys Gly Asp Ser Met Ser Leu Val Phe Tyr Ala
465                 470                 475                 480 aag ctg ctc tcg atc ctc acc gag ctg cgt acg ctg ggc aac cag aac      1488
Lys Leu Leu Ser Ile Leu Thr Glu Leu Arg Thr Leu Gly Asn Gln Asn
                485                 490                 495 gcc gag atg tgt ttc tca cta aag ctc aaa aac cgc aaa ctg ccc aag      1536
Ala Glu Met Cys Phe Ser Leu Lys Leu Lys Asn Arg Lys Leu Pro Lys
            500                 505                 510 ttc ctc gag gag atc tgg gac gtt cat gcc atc ccg cca tcg gtc cag      1584
Phe Leu Glu Glu Ile Trp Asp Val His Ala Ile Pro Pro Ser Val Gln
        515                 520                 525 tcg cac ctt cag att acc cag gag gag aac gag cgt ctc gag cgg gct      1632
Ser His Leu Gln Ile Thr Gln Glu Glu Asn Glu Arg Leu Glu Arg Ala
    530                 535                 540 gag cgt atg cgg gca tcg gtt ggg ggc gcc att acc gcc ggc att gat      1680
Glu Arg Met Arg Ala Ser Val Gly Gly Ala Ile Thr Ala Gly Ile Asp
545                 550                 555                 560 tgc gac tct gcc tcc act tcg gcg gcg gca gcc gcg gcc cag cat cag      1728
Cys Asp Ser Ala Ser Thr Ser Ala Ala Ala Ala Ala Ala Gln His Gln
                565                 570                 575 cct cag cct cag ccc cag ccc caa ccc tcc tcc ctg acc cag aac gat      1776
Pro Gln Pro Gln Pro Gln Pro Gln Pro Ser Ser Leu Thr Gln Asn Asp
            580                 585                 590 tcc cag cac cag aca cag ccg cag cta caa cct cag cta cca cct cag      1824
Ser Gln His Gln Thr Gln Pro Gln Leu Gln Pro Gln Leu Pro Pro Gln
        595                 600                 605 ctg caa ggt caa ctg caa ccc cag ctc caa cca cag ctt cag acg caa      1872
Leu Gln Gly Gln Leu Gln Pro Gln Leu Gln Pro Gln Leu Gln Thr Gln
    610                 615                 620 ctc cag cca cag att caa cca cag cca cag ctc ctt ccc gtc tcc gct      1920
Leu Gln Pro Gln Ile Gln Pro Gln Pro Gln Leu Leu Pro Val Ser Ala
625                 630                 635                 640 ccc gtg ccc gcc tcc gta acc gca cct ggt tcc ttg tcc gcg gtc agt      1968
Pro Val Pro Ala Ser Val Thr Ala Pro Gly Ser Leu Ser Ala Val Ser
                645                 650                 655 acg agc agc gaa tac atg ggc gga agt gcg gcc ata gga ccc atc acg      2016
Thr Ser Ser Glu Tyr Met Gly Gly Ser Ala Ala Ile Gly Pro Ile Thr
            660                 665                 670 ccg gca acc acc agc agt atc acg gct gcc gtt acc gct agc tcc acc      2064
Pro Ala Thr Thr Ser Ser Ile Thr Ala Ala Val Thr Ala Ser Ser Thr
        675                 680                 685 aca tca gcg gta ccg atg ggc aac gga gtt gga gtc ggt gtt ggg gtg      2112
Thr Ser Ala Val Pro Met Gly Asn Gly Val Gly Val Gly Val Gly Val
    690                 695                 700 ggc ggc aac gtc agc atg tat gcg aac gcc cag acg gcg atg gcc ttg      2160
Gly Gly Asn Val Ser Met Tyr Ala Asn Ala Gln Thr Ala Met Ala Leu
705                 710                 715                 720 atg ggt gta gcc ctg cat tcg cac caa gag cag ctt atc ggg gga gtg      2208
Met Gly Val Ala Leu His Ser His Gln Glu Gln Leu Ile Gly Gly Val
                725                 730                 735 gcg gtt aag tcg gag cac tcg acg act gca tag                          2241
Ala Val Lys Ser Glu His Ser Thr Thr Ala
            740                 745
```

```
<210> SEQ ID NO 7
<211> LENGTH: 746
<212> TYPE: PRT
<213> ORGANISM: Artificial Sequence
<220> FEATURE:
<223> OTHER INFORMATION: Description of Artificial Sequence: Recombinant
      VpEcR

<400> SEQUENCE: 7
```

| | | | | | | | | | | | | | | | |
|---|---|---|---|---|---|---|---|---|---|---|---|---|---|---|---|
| Met | Ala | Pro | Pro | Thr | Asp | Val | Ser | Leu | Gly | Asp | Glu | Leu | His | Leu | Asp |
| 1 | | | | 5 | | | | | 10 | | | | | 15 | |
| Gly | Glu | Asp | Val | Ala | Met | Ala | His | Ala | Asp | Ala | Leu | Asp | Asp | Phe | Asp |
| | | | 20 | | | | | 25 | | | | | 30 | | |
| Leu | Asp | Met | Leu | Gly | Asp | Gly | Asp | Ser | Pro | Gly | Pro | Gly | Phe | Thr | Pro |
| | | | 35 | | | | | 40 | | | | | 45 | | |
| His | Asp | Ser | Ala | Pro | Tyr | Gly | Ala | Leu | Asp | Met | Ala | Asp | Phe | Glu | Phe |
| | | 50 | | | | | 55 | | | | | 60 | | | |
| Glu | Gln | Met | Phe | Thr | Asp | Ala | Leu | Gly | Ile | Asp | Glu | Tyr | Gly | Gly | Lys |
| 65 | | | | | 70 | | | | | 75 | | | | | 80 |
| Leu | Leu | Gly | Thr | Ser | Arg | Arg | Ile | Ser | Asn | Ser | Ile | Ser | Ser | Gly | Arg |
| | | | | 85 | | | | | 90 | | | | | 95 | |
| Asp | Asp | Leu | Ser | Pro | Ser | Ser | Leu | Asn | Gly | Tyr | Ser | Ala | Asn | Glu | |
| | | | 100 | | | | | 105 | | | | | 110 | | |
| Ser | Cys | Asp | Ala | Lys | Ser | Lys | Lys | Gly | Pro | Ala | Pro | Arg | Val | Gln | |
| | | | 115 | | | | | 120 | | | | | 125 | | |
| Glu | Glu | Leu | Cys | Leu | Val | Cys | Gly | Asp | Arg | Ala | Ser | Gly | Tyr | His | Tyr |
| | | | 130 | | | | | 135 | | | | | 140 | | |
| Asn | Ala | Leu | Thr | Cys | Glu | Gly | Cys | Lys | Gly | Phe | Phe | Arg | Arg | Ser | Val |
| 145 | | | | | 150 | | | | | 155 | | | | | 160 |
| Thr | Lys | Ser | Ala | Val | Tyr | Cys | Cys | Lys | Phe | Gly | Arg | Ala | Cys | Glu | Met |
| | | | | 165 | | | | | 170 | | | | | 175 | |
| Asp | Met | Tyr | Met | Arg | Arg | Lys | Cys | Gln | Glu | Cys | Arg | Leu | Lys | Lys | Cys |
| | | | 180 | | | | | 185 | | | | | 190 | | |
| Leu | Ala | Val | Gly | Met | Arg | Pro | Glu | Cys | Val | Val | Pro | Glu | Asn | Gln | Cys |
| | | | 195 | | | | | 200 | | | | | 205 | | |
| Ala | Met | Lys | Arg | Arg | Glu | Lys | Lys | Ala | Gln | Lys | Glu | Lys | Asp | Lys | Met |
| | | 210 | | | | | 215 | | | | | 220 | | | |
| Thr | Thr | Ser | Pro | Ser | Ser | Gln | His | Gly | Gly | Asn | Gly | Ser | Leu | Ala | Ser |
| 225 | | | | | 230 | | | | | 235 | | | | | 240 |
| Gly | Gly | Gly | Gln | Asp | Phe | Val | Lys | Lys | Glu | Ile | Leu | Asp | Leu | Met | Thr |
| | | | | 245 | | | | | 250 | | | | | 255 | |
| Cys | Glu | Pro | Pro | Gln | His | Ala | Thr | Ile | Pro | Leu | Leu | Pro | Asp | Glu | Ile |
| | | | 260 | | | | | 265 | | | | | 270 | | |
| Leu | Ala | Lys | Cys | Gln | Ala | Arg | Asn | Ile | Pro | Ser | Leu | Thr | Tyr | Asn | Gln |
| | | | 275 | | | | | 280 | | | | | 285 | | |
| Leu | Ala | Val | Ile | Tyr | Lys | Leu | Ile | Trp | Tyr | Gln | Asp | Gly | Tyr | Glu | Gln |
| | | 290 | | | | | 295 | | | | | 300 | | | |
| Pro | Ser | Glu | Glu | Asp | Leu | Arg | Arg | Ile | Met | Ser | Gln | Pro | Asp | Glu | Asn |
| 305 | | | | | 310 | | | | | 315 | | | | | 320 |
| Glu | Ser | Gln | Thr | Asp | Val | Ser | Phe | Arg | His | Ile | Thr | Glu | Ile | Thr | Ile |
| | | | | 325 | | | | | 330 | | | | | 335 | |
| Leu | Thr | Val | Gln | Leu | Ile | Val | Glu | Phe | Ala | Lys | Gly | Leu | Pro | Ala | Phe |
| | | | 340 | | | | | 345 | | | | | 350 | | |
| Thr | Lys | Ile | Pro | Gln | Glu | Asp | Gln | Ile | Thr | Leu | Leu | Lys | Ala | Cys | Ser |
| | | 355 | | | | | 360 | | | | | 365 | | | |

```
Ser Glu Val Met Met Leu Arg Met Ala Arg Arg Tyr Asp His Ser Ser
    370                 375                 380
Asp Ser Ile Phe Phe Ala Asn Asn Arg Ser Tyr Thr Arg Asp Ser Tyr
385                 390                 395                 400
Lys Met Ala Gly Met Ala Asp Asn Ile Glu Asp Leu Leu His Phe Cys
                405                 410                 415
Arg Gln Met Phe Ser Met Lys Val Asp Asn Val Glu Tyr Ala Leu Leu
                420                 425                 430
Thr Ala Ile Val Ile Phe Ser Asp Arg Pro Gly Leu Glu Lys Ala Gln
            435                 440                 445
Leu Val Glu Ala Ile Gln Ser Tyr Tyr Ile Asp Thr Leu Arg Ile Tyr
    450                 455                 460
Ile Leu Asn Arg His Cys Gly Asp Ser Met Ser Leu Val Phe Tyr Ala
465                 470                 475                 480
Lys Leu Leu Ser Ile Leu Thr Glu Leu Arg Thr Leu Gly Asn Gln Asn
                485                 490                 495
Ala Glu Met Cys Phe Ser Leu Lys Leu Lys Asn Arg Lys Leu Pro Lys
                500                 505                 510
Phe Leu Glu Glu Ile Trp Asp Val His Ala Ile Pro Pro Ser Val Gln
    515                 520                 525
Ser His Leu Gln Ile Thr Gln Glu Asn Glu Arg Leu Glu Arg Ala
    530                 535                 540
Glu Arg Met Arg Ala Ser Val Gly Gly Ala Ile Thr Ala Gly Ile Asp
545                 550                 555                 560
Cys Asp Ser Ala Ser Thr Ser Ala Ala Ala Ala Ala Gln His Gln
                565                 570                 575
Pro Gln Pro Gln Pro Gln Pro Gln Ser Ser Leu Thr Gln Asn Asp
                580                 585                 590
Ser Gln His Gln Thr Gln Pro Gln Leu Gln Pro Gln Leu Pro Pro Gln
    595                 600                 605
Leu Gln Gly Gln Leu Gln Pro Gln Leu Gln Pro Gln Leu Gln Thr Gln
    610                 615                 620
Leu Gln Pro Gln Ile Gln Pro Gln Leu Leu Pro Val Ser Ala
625                 630                 635                 640
Pro Val Pro Ala Ser Val Thr Ala Pro Gly Ser Leu Ser Ala Val Ser
                645                 650                 655
Thr Ser Ser Glu Tyr Met Gly Gly Ser Ala Ala Ile Gly Pro Ile Thr
                660                 665                 670
Pro Ala Thr Thr Ser Ser Ile Thr Ala Ala Val Thr Ala Ser Ser Thr
            675                 680                 685
Thr Ser Ala Val Pro Met Gly Asn Gly Val Gly Val Gly Val Gly Val
    690                 695                 700
Gly Gly Asn Val Ser Met Tyr Ala Asn Ala Gln Thr Ala Met Ala Leu
705                 710                 715                 720
Met Gly Val Ala Leu His Ser His Gln Glu Gln Leu Ile Gly Gly Val
                725                 730                 735
Ala Val Lys Ser Glu His Ser Thr Thr Ala
                740                 745

<210> SEQ ID NO 8
<211> LENGTH: 3126
<212> TYPE: DNA
<213> ORGANISM: Artificial Sequence
<220> FEATURE:
```

<223> OTHER INFORMATION: Description of Artificial Sequence: Recombinant
      GEcR
<221> NAME/KEY: CDS
<222> LOCATION: (1)..(3123)

<400> SEQUENCE: 8

```
atg gac tcc aaa gaa tca tta act cct ggt aga gaa gaa aac ccc agc      48
Met Asp Ser Lys Glu Ser Leu Thr Pro Gly Arg Glu Glu Asn Pro Ser
 1               5                  10                  15 agt gtg ctt gct cag gag agg gga gat gtg atg gac ttc tat aaa acc      96
Ser Val Leu Ala Gln Glu Arg Gly Asp Val Met Asp Phe Tyr Lys Thr
             20                  25                  30 cta aga gga gga gct act gtg aag gtt tct gcg tct tca ccc tca ctg     144
Leu Arg Gly Gly Ala Thr Val Lys Val Ser Ala Ser Ser Pro Ser Leu
         35                  40                  45 gct gtc gct tct caa tca gac tcc aag cag cga aga ctt ttg gtt gat     192
Ala Val Ala Ser Gln Ser Asp Ser Lys Gln Arg Arg Leu Leu Val Asp
     50                  55                  60 ttt cca aaa ggc tca gta agc aat gcg cag cag cca gat ctg tcc aaa     240
Phe Pro Lys Gly Ser Val Ser Asn Ala Gln Gln Pro Asp Leu Ser Lys
 65                  70                  75                  80 gca gtt tca ctc tca atg gga ctg tat atg gga gag aca gaa aca aaa     288
Ala Val Ser Leu Ser Met Gly Leu Tyr Met Gly Glu Thr Glu Thr Lys
                 85                  90                  95 gtg atg gga aat gac ctg gga ttc cca cag cag ggc caa atc agc ctt     336
Val Met Gly Asn Asp Leu Gly Phe Pro Gln Gln Gly Gln Ile Ser Leu
            100                 105                 110 tcc tcg ggg gaa aca gac tta aag ctt ttg gaa gaa agc att gca aac     384
Ser Ser Gly Glu Thr Asp Leu Lys Leu Leu Glu Glu Ser Ile Ala Asn
        115                 120                 125 ctc aat agg tcg acc agt gtt cca gag aac ccc aag agt tca gca tcc     432
Leu Asn Arg Ser Thr Ser Val Pro Glu Asn Pro Lys Ser Ser Ala Ser
    130                 135                 140 act gct gtg tct gct gcc ccc aca gag aag gag ttt cca aaa act cac     480
Thr Ala Val Ser Ala Ala Pro Thr Glu Lys Glu Phe Pro Lys Thr His
145                 150                 155                 160 tct gat gta tct tca gaa cag caa cat ttg aag ggc cag act ggc acc     528
Ser Asp Val Ser Ser Glu Gln Gln His Leu Lys Gly Gln Thr Gly Thr
                165                 170                 175 aac ggt ggc aat gtg aaa ttg tat acc aca gac caa agc acc ttt gac     576
Asn Gly Gly Asn Val Lys Leu Tyr Thr Thr Asp Gln Ser Thr Phe Asp
            180                 185                 190 att ttg cag gat ttg gag ttt tct tct ggg tcc cca ggt aaa gag acg     624
Ile Leu Gln Asp Leu Glu Phe Ser Ser Gly Ser Pro Gly Lys Glu Thr
        195                 200                 205 aat gag agt cct tgg aga tca gac ctg ttg ata gat gaa aac tgt ttg     672
Asn Glu Ser Pro Trp Arg Ser Asp Leu Leu Ile Asp Glu Asn Cys Leu
    210                 215                 220 ctt tct cct ctg gcg gga gaa gac gat tca ttc ctt ttg gaa gga aac     720
Leu Ser Pro Leu Ala Gly Glu Asp Asp Ser Phe Leu Leu Glu Gly Asn
225                 230                 235                 240 tcg aat gag gac tgc aag cct ctc att tta ccg gac act aaa ccc aaa     768
Ser Asn Glu Asp Cys Lys Pro Leu Ile Leu Pro Asp Thr Lys Pro Lys
                245                 250                 255 att aag gat aat gga gat ctg gtt ttg tca agc ccc agt aat gta aca     816
Ile Lys Asp Asn Gly Asp Leu Val Leu Ser Ser Pro Ser Asn Val Thr
            260                 265                 270 ctg ccc caa gtg aaa aca gaa aaa gaa gat ttc atc gaa ctc tgc acc     864
Leu Pro Gln Val Lys Thr Glu Lys Glu Asp Phe Ile Glu Leu Cys Thr
        275                 280                 285
```

```
cct ggg gta att aag caa gag aaa ctg ggc aca gtt tac tgt cag gca      912
Pro Gly Val Ile Lys Gln Glu Lys Leu Gly Thr Val Tyr Cys Gln Ala
    290                 295                 300 agc ttt cct gga gca aat ata att ggt aat aaa atg tct gcc att tct      960
Ser Phe Pro Gly Ala Asn Ile Ile Gly Asn Lys Met Ser Ala Ile Ser
305                 310                 315                 320 gtt cat ggt gtg agt acc tct gga gga cag atg tac cac tat gac atg     1008
Val His Gly Val Ser Thr Ser Gly Gly Gln Met Tyr His Tyr Asp Met
                325                 330                 335 aat aca gca tcc ctt tct caa cag cag gat cag aag cct att ttt aat     1056
Asn Thr Ala Ser Leu Ser Gln Gln Gln Asp Gln Lys Pro Ile Phe Asn
            340                 345                 350 gtc att cca cca att ccc gtt ggt tcc gaa aat tgg aat agg tgc caa     1104
Val Ile Pro Pro Ile Pro Val Gly Ser Glu Asn Trp Asn Arg Cys Gln
        355                 360                 365 gga tct gga gat gac aac ttg act tct ctg ggg act ctg aac ttc cct     1152
Gly Ser Gly Asp Asp Asn Leu Thr Ser Leu Gly Thr Leu Asn Phe Pro
370                 375                 380 ggt cga aca gtt ttt tct aat ggc tat tca agc ccc agc atg aga cca     1200
Gly Arg Thr Val Phe Ser Asn Gly Tyr Ser Ser Pro Ser Met Arg Pro
385                 390                 395                 400 gat gta agc tct cct cca tcc agc tcc tca aca gca aca aca gga cca     1248
Asp Val Ser Ser Pro Pro Ser Ser Ser Thr Ala Thr Thr Gly Pro
                405                 410                 415 cct ccc agc ggc cgc gtg caa gag gag ctg tgc ctg gtt tgc ggc gac     1296
Pro Pro Ser Gly Arg Val Gln Glu Glu Leu Cys Leu Val Cys Gly Asp
            420                 425                 430 agg gcc tcc ggc tac cac tac aac gcc ctc acc tgt gga tcc tgc aag     1344
Arg Ala Ser Gly Tyr His Tyr Asn Ala Leu Thr Cys Gly Ser Cys Lys
        435                 440                 445 gtg ttc ttt cga cgc agc gtt acg aag agc gcc gtc tac tgc tgc aag     1392
Val Phe Phe Arg Arg Ser Val Thr Lys Ser Ala Val Tyr Cys Cys Lys
450                 455                 460 ttc ggg cgc gcc tgc gaa atg gac atg tac atg agg cga aag tgt cag     1440
Phe Gly Arg Ala Cys Glu Met Asp Met Tyr Met Arg Arg Lys Cys Gln
465                 470                 475                 480 gag tgc cgc ctg aaa aag tgc ctg gcc gtg ggt atg cgg ccg gaa tgc     1488
Glu Cys Arg Leu Lys Lys Cys Leu Ala Val Gly Met Arg Pro Glu Cys
                485                 490                 495 gtc gtc ccg gag aac caa tgt gcg atg aag cgg cgc gaa aag aag gcc     1536
Val Val Pro Glu Asn Gln Cys Ala Met Lys Arg Arg Glu Lys Lys Ala
            500                 505                 510 cag aag gag aag gac aaa atg acc act tcg ccg agc tct cag cat ggc     1584
Gln Lys Glu Lys Asp Lys Met Thr Thr Ser Pro Ser Ser Gln His Gly
        515                 520                 525 ggc aat ggc agc ttg gcc tct ggt ggc ggc caa gac ttt gtt aag aag     1632
Gly Asn Gly Ser Leu Ala Ser Gly Gly Gly Gln Asp Phe Val Lys Lys
530                 535                 540 gag att ctt gac ctt atg aca tgc gag ccg ccc cag cat gcc act att     1680
Glu Ile Leu Asp Leu Met Thr Cys Glu Pro Pro Gln His Ala Thr Ile
545                 550                 555                 560 ccg cta cta cct gat gaa ata ttg gcc aag tgt caa gcg cgc aat ata     1728
Pro Leu Leu Pro Asp Glu Ile Leu Ala Lys Cys Gln Ala Arg Asn Ile
                565                 570                 575 cct tcc tta acg tac aat cag ttg gcc gtt ata tac aag tta att tgg     1776
Pro Ser Leu Thr Tyr Asn Gln Leu Ala Val Ile Tyr Lys Leu Ile Trp
            580                 585                 590 tac cag gat ggc tat gag cag cca tct gaa gag gat ctc agg cgt ata     1824
Tyr Gln Asp Gly Tyr Glu Gln Pro Ser Glu Glu Asp Leu Arg Arg Ile
        595                 600                 605
```

-continued

| | | |
|---|---|---|
| atg agt caa ccc gat gag aac gag agc caa acg gac gtc agc ttt cgg<br>Met Ser Gln Pro Asp Glu Asn Glu Ser Gln Thr Asp Val Ser Phe Arg<br>610              615                  620 | | 1872 |
| cat ata acc gag ata acc ata ctc acg gtc cag ttg att gtt gag ttt<br>His Ile Thr Glu Ile Thr Ile Leu Thr Val Gln Leu Ile Val Glu Phe<br>625              630                  635                  640 | | 1920 |
| gct aaa ggt cta cca gcg ttt aca aag ata ccc cag gag gac cag atc<br>Ala Lys Gly Leu Pro Ala Phe Thr Lys Ile Pro Gln Glu Asp Gln Ile<br>              645                  650                  655 | | 1968 |
| acg tta cta aag gcc tgc tcg tcg gag gtg atg atg ctg cgt atg gca<br>Thr Leu Leu Lys Ala Cys Ser Ser Glu Val Met Met Leu Arg Met Ala<br>              660                  665                  670 | | 2016 |
| cga cgc tat gac cac agc tcg gac tca ata ttc ttc gcg aat aat aga<br>Arg Arg Tyr Asp His Ser Ser Asp Ser Ile Phe Phe Ala Asn Asn Arg<br>              675                  680                  685 | | 2064 |
| tca tat acg cgg gat tct tac aaa atg gcc gga atg gct gat aac att<br>Ser Tyr Thr Arg Asp Ser Tyr Lys Met Ala Gly Met Ala Asp Asn Ile<br>              690                  695                  700 | | 2112 |
| gaa gac ctg ctg cat ttc tgc cgc caa atg ttc tcg atg aag gtg gac<br>Glu Asp Leu Leu His Phe Cys Arg Gln Met Phe Ser Met Lys Val Asp<br>705              710                  715                  720 | | 2160 |
| aac gtc gaa tac gcg ctt ctc act gcc att gtg atc ttc tcg gac cgg<br>Asn Val Glu Tyr Ala Leu Leu Thr Ala Ile Val Ile Phe Ser Asp Arg<br>              725                  730                  735 | | 2208 |
| ccg ggc ctg gag aag gcc caa cta gtc gaa gcg atc cag agc tac tac<br>Pro Gly Leu Glu Lys Ala Gln Leu Val Glu Ala Ile Gln Ser Tyr Tyr<br>              740                  745                  750 | | 2256 |
| atc gac acg cta cgc att tat ata ctc aac cgc cac tgc ggc gac tca<br>Ile Asp Thr Leu Arg Ile Tyr Ile Leu Asn Arg His Cys Gly Asp Ser<br>              755                  760                  765 | | 2304 |
| atg agc ctc gtc ttc tac gca aag ctg ctc tcg atc ctc acc gag ctg<br>Met Ser Leu Val Phe Tyr Ala Lys Leu Leu Ser Ile Leu Thr Glu Leu<br>              770                  775                  780 | | 2352 |
| cgt acg ctg ggc aac cag aac gcc gag atg tgt ttc tca cta aag ctc<br>Arg Thr Leu Gly Asn Gln Asn Ala Glu Met Cys Phe Ser Leu Lys Leu<br>785              790                  795                  800 | | 2400 |
| aaa aac cgc aaa ctg ccc aag ttc ctc gag gag atc tgg gac gtt cat<br>Lys Asn Arg Lys Leu Pro Lys Phe Leu Glu Glu Ile Trp Asp Val His<br>              805                  810                  815 | | 2448 |
| gcc atc ccg cca tcg gtc cag tcg cac ctt cag att acc cag gag gag<br>Ala Ile Pro Pro Ser Val Gln Ser His Leu Gln Ile Thr Gln Glu Glu<br>              820                  825                  830 | | 2496 |
| aac gag cgt ctc gag cgg gct gag cgt atg cgg gca tcg gtt ggg ggc<br>Asn Glu Arg Leu Glu Arg Ala Glu Arg Met Arg Ala Ser Val Gly Gly<br>835              840                  845 | | 2544 |
| gcc att acc gcc ggc att gat tgc gac tct gcc tcc act tcg gcg gcg<br>Ala Ile Thr Ala Gly Ile Asp Cys Asp Ser Ala Ser Thr Ser Ala Ala<br>850              855                  860 | | 2592 |
| gca gcc gcg gcc cag cat cag cct cag cct cag ccc cag ccc caa ccc<br>Ala Ala Ala Ala Gln His Gln Pro Gln Pro Gln Pro Gln Pro Gln Pro<br>865              870                  875                  880 | | 2640 |
| tcc tcc ctg acc cag aac gat tcc cag cac cag aca cag ccg cag cta<br>Ser Ser Leu Thr Gln Asn Asp Ser Gln His Gln Thr Gln Pro Gln Leu<br>              885                  890                  895 | | 2688 |
| caa cct cag cta cca cct cag ctg caa ggt caa ctg caa ccc cag ctc<br>Gln Pro Gln Leu Pro Pro Gln Leu Gln Gly Gln Leu Gln Pro Gln Leu<br>              900                  905                  910 | | 2736 |
| caa cca cag ctt cag acg caa ctc cag cca cag att caa cca cag cca<br>Gln Pro Gln Leu Gln Thr Gln Leu Gln Pro Gln Ile Gln Pro Gln Pro | | 2784 |

-continued

```
                915                 920                 925
cag ctc ctt ccc gtc tcc gct ccc gtg ccc gcc tcc gta acc gca cct      2832
Gln Leu Leu Pro Val Ser Ala Pro Val Pro Ala Ser Val Thr Ala Pro
    930                 935                 940 ggt tcc ttg tcc gcg gtc agt acg agc agc gaa tac atg ggc gga agt      2880
Gly Ser Leu Ser Ala Val Ser Thr Ser Ser Glu Tyr Met Gly Gly Ser
945                 950                 955                 960 gcg gcc ata gga ccc atc acg ccg gca acc acc agc agt atc acg gct      2928
Ala Ala Ile Gly Pro Ile Thr Pro Ala Thr Thr Ser Ser Ile Thr Ala
                965                 970                 975 gcc gtt acc gct agc tcc acc aca tca gcg gta ccg atg ggc aac gga      2976
Ala Val Thr Ala Ser Ser Thr Thr Ser Ala Val Pro Met Gly Asn Gly
            980                 985                 990 gtt gga gtc ggt gtt ggg gtg ggc ggc aac gtc agc atg tat gcg aac      3024
Val Gly Val Gly Val Gly Val Gly Gly Asn Val Ser Met Tyr Ala Asn
        995                 1000                1005 gcc cag acg gcg atg gcc ttg atg ggt gta gcc ctg cat tcg cac caa      3072
Ala Gln Thr Ala Met Ala Leu Met Gly Val Ala Leu His Ser His Gln
    1010                1015                1020 gag cag ctt atc ggg gga gtg gcg gtt aag tcg gag cac tcg acg act      3120
Glu Gln Leu Ile Gly Gly Val Ala Val Lys Ser Glu His Ser Thr Thr
1025                1030                1035                1040 gca tag                                                               3126
Ala
```

<210> SEQ ID NO 9
<211> LENGTH: 1041
<212> TYPE: PRT
<213> ORGANISM: Artificial Sequence
<220> FEATURE:
<223> OTHER INFORMATION: Description of Artificial Sequence: Recombinant GEcR

<400> SEQUENCE: 9

```
Met Asp Ser Lys Glu Ser Leu Thr Pro Gly Arg Glu Glu Asn Pro Ser
  1               5                  10                  15

Ser Val Leu Ala Gln Glu Arg Gly Asp Val Met Asp Phe Tyr Lys Thr
             20                  25                  30

Leu Arg Gly Gly Ala Thr Val Lys Val Ser Ala Ser Ser Pro Ser Leu
         35                  40                  45

Ala Val Ala Ser Gln Ser Asp Ser Lys Gln Arg Arg Leu Leu Val Asp
     50                  55                  60

Phe Pro Lys Gly Ser Val Ser Asn Ala Gln Gln Pro Asp Leu Ser Lys
 65                  70                  75                  80

Ala Val Ser Leu Ser Met Gly Leu Tyr Met Gly Glu Thr Glu Thr Lys
                 85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190
```

-continued

```
Ile Leu Gln Asp Leu Glu Phe Ser Ser Gly Pro Gly Lys Glu Thr
        195                 200                 205

Asn Glu Ser Pro Trp Arg Ser Asp Leu Leu Ile Asp Glu Asn Cys Leu
        210                 215                 220

Leu Ser Pro Leu Ala Gly Glu Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
                260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
        290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Asp Gln Lys Pro Ile Phe Asn
        340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
        370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Ser Gly Arg Val Gln Glu Glu Leu Cys Leu Val Cys Gly Asp
                420                 425                 430

Arg Ala Ser Gly Tyr His Tyr Asn Ala Leu Thr Cys Gly Ser Cys Lys
        435                 440                 445

Val Phe Phe Arg Arg Ser Val Thr Lys Ser Ala Val Tyr Cys Cys Lys
        450                 455                 460

Phe Gly Arg Ala Cys Glu Met Asp Met Tyr Met Arg Arg Lys Cys Gln
465                 470                 475                 480

Glu Cys Arg Leu Lys Lys Cys Leu Ala Val Gly Met Arg Pro Glu Cys
                485                 490                 495

Val Val Pro Glu Asn Gln Cys Ala Met Lys Arg Arg Glu Lys Lys Ala
                500                 505                 510

Gln Lys Glu Lys Asp Lys Met Thr Thr Ser Pro Ser Ser Gln His Gly
        515                 520                 525

Gly Asn Gly Ser Leu Ala Ser Gly Gly Gly Gln Asp Phe Val Lys Lys
        530                 535                 540

Glu Ile Leu Asp Leu Met Thr Cys Glu Pro Pro Gln His Ala Thr Ile
545                 550                 555                 560

Pro Leu Leu Pro Asp Glu Ile Leu Ala Lys Cys Gln Ala Arg Asn Ile
                565                 570                 575

Pro Ser Leu Thr Tyr Asn Gln Leu Ala Val Ile Tyr Lys Leu Ile Trp
                580                 585                 590

Tyr Gln Asp Gly Tyr Glu Gln Pro Ser Glu Glu Asp Leu Arg Arg Ile
        595                 600                 605
```

```
Met Ser Gln Pro Asp Glu Asn Glu Ser Gln Thr Asp Val Ser Phe Arg
610                 615                 620
His Ile Thr Glu Ile Thr Ile Leu Thr Val Gln Leu Ile Val Glu Phe
625                 630                 635                 640
Ala Lys Gly Leu Pro Ala Phe Thr Lys Ile Pro Gln Glu Asp Gln Ile
                645                 650                 655
Thr Leu Leu Lys Ala Cys Ser Ser Glu Val Met Met Leu Arg Met Ala
                660                 665                 670
Arg Arg Tyr Asp His Ser Ser Asp Ser Ile Phe Phe Ala Asn Asn Arg
            675                 680                 685
Ser Tyr Thr Arg Asp Ser Tyr Lys Met Ala Gly Met Ala Asp Asn Ile
        690                 695                 700
Glu Asp Leu Leu His Phe Cys Arg Gln Met Phe Ser Met Lys Val Asp
705                 710                 715                 720
Asn Val Glu Tyr Ala Leu Leu Thr Ala Ile Val Ile Phe Ser Asp Arg
                725                 730                 735
Pro Gly Leu Glu Lys Ala Gln Leu Val Glu Ala Ile Gln Ser Tyr Tyr
                740                 745                 750
Ile Asp Thr Leu Arg Ile Tyr Ile Leu Asn Arg His Cys Gly Asp Ser
            755                 760                 765
Met Ser Leu Val Phe Tyr Ala Lys Leu Leu Ser Ile Leu Thr Glu Leu
        770                 775                 780
Arg Thr Leu Gly Asn Gln Asn Ala Glu Met Cys Phe Ser Leu Lys Leu
785                 790                 795                 800
Lys Asn Arg Lys Leu Pro Lys Phe Leu Glu Glu Ile Trp Asp Val His
                805                 810                 815
Ala Ile Pro Pro Ser Val Gln Ser His Leu Gln Ile Thr Gln Glu Glu
                820                 825                 830
Asn Glu Arg Leu Glu Arg Ala Glu Arg Met Arg Ala Ser Val Gly Gly
            835                 840                 845
Ala Ile Thr Ala Gly Ile Asp Cys Asp Ser Ala Ser Thr Ser Ala Ala
        850                 855                 860
Ala Ala Ala Gln His Gln Pro Gln Pro Gln Pro Gln Pro Gln Pro Gln
865                 870                 875                 880
Ser Ser Leu Thr Gln Asn Asp Ser Gln His Gln Thr Gln Pro Gln Leu
                885                 890                 895
Gln Pro Gln Leu Pro Pro Gln Leu Gln Gly Gln Leu Gln Pro Gln Leu
                900                 905                 910
Gln Pro Gln Leu Gln Thr Gln Leu Gln Pro Gln Ile Gln Pro Gln Pro
            915                 920                 925
Gln Leu Leu Pro Val Ser Ala Pro Val Pro Ala Ser Val Thr Ala Pro
        930                 935                 940
Gly Ser Leu Ser Ala Val Ser Thr Ser Ser Glu Tyr Met Gly Gly Ser
945                 950                 955                 960
Ala Ala Ile Gly Pro Ile Thr Pro Ala Thr Thr Ser Ser Ile Thr Ala
                965                 970                 975
Ala Val Thr Ala Ser Ser Thr Thr Ser Ala Val Pro Met Gly Asn Gly
                980                 985                 990
Val Gly Val Gly Val Gly Val Gly Asn Val Ser Met Tyr Ala Asn
            995                 1000                1005
Ala Gln Thr Ala Met Ala Leu Met Gly Val Ala Leu His Ser His Gln
    1010                1015                1020
Glu Gln Leu Ile Gly Gly Val Ala Val Lys Ser Glu His Ser Thr Thr
```

```
                1025          1030          1035          1040
Ala

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Modified
      ecdysone response element
<221> NAME/KEY: modified_base
<222> LOCATION: (4)..(5)
<223> OTHER INFORMATION: a, c, t, g, other or unknown
<221> NAME/KEY: modified_base
<222> LOCATION: (7)..(11)
<223> OTHER INFORMATION: a, c, t, g, other or unknown, wherein the
      length of this region may vary in length from 0 to 5, with 1
      being especially preferred
<221> NAME/KEY: modified_base
<222> LOCATION: (14)..(15)
<223> OTHER INFORMATION: a, c, t, g, other or unknown

<400> SEQUENCE: 10
rgbnnmnnnn ntgnncy                                              17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Modified
      ecdysone response element
<221> NAME/KEY: modified_base
<222> LOCATION: (3)..(4)
<223> OTHER INFORMATION: a, c, t, g, other or unknown
<221> NAME/KEY: modified_base
<222> LOCATION: (7)..(11)
<223> OTHER INFORMATION: a, c, t, g, other or unknown, wherein the
      length of this region may vary in length from 0 to 5, with 1
      being especially preferred
<221> NAME/KEY: modified_base
<222> LOCATION: (13)..(14)
<223> OTHER INFORMATION: a, c, t, g, other or unknown

<400> SEQUENCE: 11
rgnncannnn nknnvcy                                              17

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Modified
      ecdysone response element
<221> NAME/KEY: modified_base
<222> LOCATION: (7)
<223> OTHER INFORMATION: a, c, t, g, other or unknown

<400> SEQUENCE: 12
agtgcantgt tct                                                  13

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Modified
      ecdysone response element
<221> NAME/KEY: modified_base
<222> LOCATION: (4)..(5)
<223> OTHER INFORMATION: a, c, t, g, other or unknown
```

```
<221> NAME/KEY: modified_base
<222> LOCATION: (7)..(11)
<223> OTHER INFORMATION: a, c, t, g, other or unknown, wherein the
      length of this region may vary in length from 0 to 5, with 3
      being especially preferred
<221> NAME/KEY: modified_base
<222> LOCATION: (15)..(16)
<223> OTHER INFORMATION: a, c, t, g, other or unknown

<400> SEQUENCE: 13
rgbnnmnnnn nrgbnnm                                                  17

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tacaacgccc tcacctgtgg atcctgcaag gtgtttcttt cgacgcagc               49

<210> SEQ ID NO 15
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtactcccgg ggcggggcta tgcggggcgg ggctaatcgc tagggcggg gca           53

<210> SEQ ID NO 16
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtactgcccc gcccctagcg attagccccg ccccgcatag ccccgccccg gga          53

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agctcgatgg acaagtgcat tgttctttgc tgaa                               34

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agctttcagc aagagaacaa tgcacttgtc catcg                              35
```

METHOD FOR MODULATING EXPRESSION OF EXOGENOUS GENES IN MAMMALIAN SYSTEMS, AND PRODUCTS RELATED THERETO

RELATED APPLICATIONS

This application is a continuation-in-part of U.S. Ser. No. 08/974,530, filed Nov. 19, 1997, now abandoned, which is, in turn, a continuation-in-part of U.S. Ser. No. 08/628,830, filed Apr. 5, 1996, now abandoned, the entire contents of both of which are hereby incorporated by reference herein.

FIELD OF THE INVENTION

The present invention relates to methods in the field of recombinant DNA technology, and products related thereto. More particularly, the invention relates to methods and products for modulating the expression of exogenous genes in mammalian systems.

BACKGROUND OF THE INVENTION

The steroid/thyroid hormone receptors comprise a superfamily of ligand-dependent transcription factors that play a crucial role in mediating changes in cell fate and function (Evans, R. M., Science 240:889–895 (1988)). The receptors transduce extracellular hormonal signals to target genes that contain specific enhancer sequences referred to as hormone response elements (HREs) Evans, (1988); Green and Chambon, Trends Genet. 4:309–314 (1988); Yamamoto, K. R., Annu. Rev. Genet. 19:209–252 (1985)). Each receptor recognizes its own HRE, assuring that a distinct response is triggered by each hormonal signal. Together the collection of related transcription factors and their cognate response elements provides a unique opportunity to control gene expression.

The DNA binding domain of each member of the steroid/thyroid hormone superfamily of receptors has 66–68 amino acids. Twenty of these, including nine cysteines, are conserved throughout the family. The modular structure of members of this receptor superfamily allows the exchange of homologous domains between receptors to create functional chimeras. This strategy was used to demonstrate that the DNA binding domain is solely responsible for the specific recognition of the HRE in vivo (Green and Chambon, Nature 325:75–78 (1987); Giguère et al., Nature 330:624–629 (1987); Petkovich et al., Nature 330:444–450 (1987); Kumar et al., Cell 51:941–951 (1987); Umesono et al., Nature 336:262–265 (1988); Thompson and Evans, Proc. Natl. Acad. Sci. U.S.A. 86:3494–3498 (1989) and in vitro (Kumar and Chambon, Cell 55:145–156 (1988)). By analogy with the proposed structure for Xenopus transcription factor IIIA (Miller et al., EMBO J. 4:1609–1614 (1985)), the invariant cysteines are thought to form two "zinc fingers" that mediate the DNA binding function (Hollenberg and Evans, Cell 55:899–906 (1988)). Involvement of these cysteines in Zn(II) coordination is supported by extended X-ray absorption fine structure (Freedman et al., Nature 334:543–546 (1988)), and DNA binding by point mutagenesis experiments (Hollenberg and Evans, (1988)); Severne et al., EMBO J. 7:2503–2508 (1988)).

The HREs are in fact structurally related but functionally distinct. The glucocorticoid receptor response element (GRE), estrogen receptor response element (ERE), and thyroid hormone receptor response element (TRE) have been characterized in detail. These particular response elements have been found to have a palindromic pair of hexameric "half-sites" (Evans, (1988); Green and Chambon, (1988)). With optimized pseudo- or consensus response elements, only two nucleotides per half-site differ between GRE and ERE (Klock et al., Nature 329:734–736 (1987)). On the other hand, EREs and TREs have identical half-sites but the number of nucleotide spacers between the two half sites is different (Glass et al., Cell 54:313–323 (1988)).

In contrast to response elements having the palindromic sequence motif, the following hormone receptors typically recognize response elements having two half-sites in a direct-repeat (DR) sequence motif: RXR, RAR, COUP-TF, PPAR, and the like (see, e.g., Mangelsdorf et al., The Retinoids: Biology, Chemistry, and Medicine, 2nd Edition, Raven Press, Ltd., New York, 1994, Chapter 8). Thus at least three distinct means are used to achieve HRE diversity: 1) binding site specificity for a particular half-site; 2) nucleotide spacing between the two half-sites; and 3) the orientation of the half-sites to one another.

In insect systems, a pulse of the steroid hormone ecdysone triggers metamorphosis in Drosophila melanogaster showing genomic effects, such as chromosomal puffing, within minutes of hormone addition. Mediating this response in insects is the functional ecdysone receptor, a heterodimer of the ecdysone receptor (EcR) and the product of the ultraspiracle gene (USP) (Yao et al. (1993) Nature 366, 476–479; and Yao et al. (1992) Cell 71, 63–72). Responsiveness to an insect ecdysteroid can be recreated in cultured mammalian cells by co-transfection of EcR, USP, an ecdysone responsive reporter, and treatment with ecdysone or the synthetic analog muristerone A.

In the field of genetic engineering, precise control of gene expression is an invaluable tool in studying, manipulating and controlling development and other physiological processes. For example applications for regulated gene expression in mammalian systems include inducible gene targeting, overexpression of toxic and teratogenic genes, anti-sense RNA expression, and gene therapy (Jaenisch, R. (1988) Science 240, 1468–1474). For cultured cells, glucocorticoids and other steroids have been used to induce the expression of a desired gene.

As another means for controlling gene expression in a mammalian system, an inducible tetracycline regulated system has been devised and utilized in transgenic mice, whereby gene activity is induced in the absence of the antibiotic and repressed in its presence (see, e.g, Gossen et al. (1992) Proc. Natl. Acad. Sci. 89, 5547–5551; Gossen et al. (1993) TIBS 18, 471–475; Furth et al. (1994) Proc. Natl. Acad. Sci. 91, 9302–9306; and Shockett et al. (1995) Proc. Natl. Acad. Sci. 92, 6522–6526). However, disadvantages of this system include the continuous treatment of tetracycline to repress expression and the slow clearance of antibiotic from bone which interferes with quick and precise induction. While this system has been improved by the recent identification of a mutant tetracycline repressor which acts conversely as an inducible activator, the pharmacokinetics of tetracycline may hinder its use during development when a precise and efficient "on-off" switch is essential (Gossen et al. (1995) Science 268, 1766–1769).

Accordingly, there is a need in the art for improved methods to precisely modulate the expression of exogenous genes in mammalian subjects.

BRIEF DESCRIPTION OF THE INVENTION

In accordance with the present invention, there are provided various methods for modulating the expression of an exogenous gene in a mammalian subject. The invention method is useful in a wide variety of applications where inducible in vivo expression of an exogenous gene is desired, such as in vivo therapeutic methods for delivering recombinant proteins into a variety of cells within a patient.

Unlike prior art tetracycline based strategies, transferring ecdysone responsiveness to mammalian cells takes advantage of a naturally evolved steroid inducible system. Advantages of ecdysteroid use include the lipophilic nature of the compounds (which provides efficient penetrance thereof into all tissues, including the brain), short half-lives (which allow for precise and potent inductions), and favorable pharmacokinetics that prevent storage and expedite clearance.

In accordance with another embodiment of the present invention, there are provided modified ecdysone receptors, which can be in the form of homodimeric species or heterodimeric species comprising at least one silent partner of the steroid/thyroid hormone superfamily of receptors, along with an invention modified ecdysone receptor. Invention modified ecdysone receptors are useful, for example, in methods for modulating expression of an exogenous gene in a mammalian subject.

In accordance with additional embodiments of the present invention, there are provided nucleic acids encoding invention modified ecdysone receptors, modified ecdysone receptor response elements, gene transfer vectors, recombinant cells, and transgenic animals containing nucleic acid encoding invention modified ecdysone receptor.

BRIEF DESCRIPTION OF THE FIGURES

In FIG. 1A, the numerical values on both sides of the figure are on the same scale, with the GEcR/RXR value repeated for clarity. Darkened and stripped bars represent reporter activity with no hormone or 1 $\mu$M muristerone A, respectively.

FIG. 1B shows FXR and VpEcR activity on ecdysone response element (EcRE) and a hybrid ecdysone/glucocorticoid response element (E/GRE) responsive reporters. VpEcR, VgEcR, and control transfection without receptors were treated with 1 $\mu$M muristerone. FXR transfections were treated with 50 $\mu$M Juvenile Hormone III (Sigma). Darkened and stripped bars represent reporter activity with no hormone or 1 $\mu$M muristerone A/50 $\mu$M Juvenile Hormone III, respectively.

FIG. 1C shows that E/GRE and GRE are non-overlapping response elements. Darkened and stripped bars represent reporter activity with no hormone or 1 $\mu$M muristerone A/1 $\mu$M dexamethasone, respectively.

FIG. 1D shows a schematic diagram of modified ecdysone receptors. GEcR is a chimeric receptor containing the N-terminal transactivation domain of GR and the DNA- and ligand-binding domains of EcR. VpEcR is an N-terminal truncation of EcR, wherein the activation domain of Vp16 is fused thereto at the amino terminus thereof. VgEcR is identical to VpEcR except for the following point mutations in the P box of the DNA binding domain: E282G, G283S, and G286V. Vp16-EcR-B1 is a fusion of full length EcR with the activation domain of Vp16, wherein the activation domain of Vp16 is fused thereto at the carboxy terminus thereof. VgEcR-B1 is identical to Vp16-EcR-B1 except for the same point mutations in the P box of the DNA binding domain as described above. In the Figure, DBD=DNA binding domain and LBD=ligand binding domain.

DETAILED DESCRIPTION OF THE INVENTION

Figure 1A:
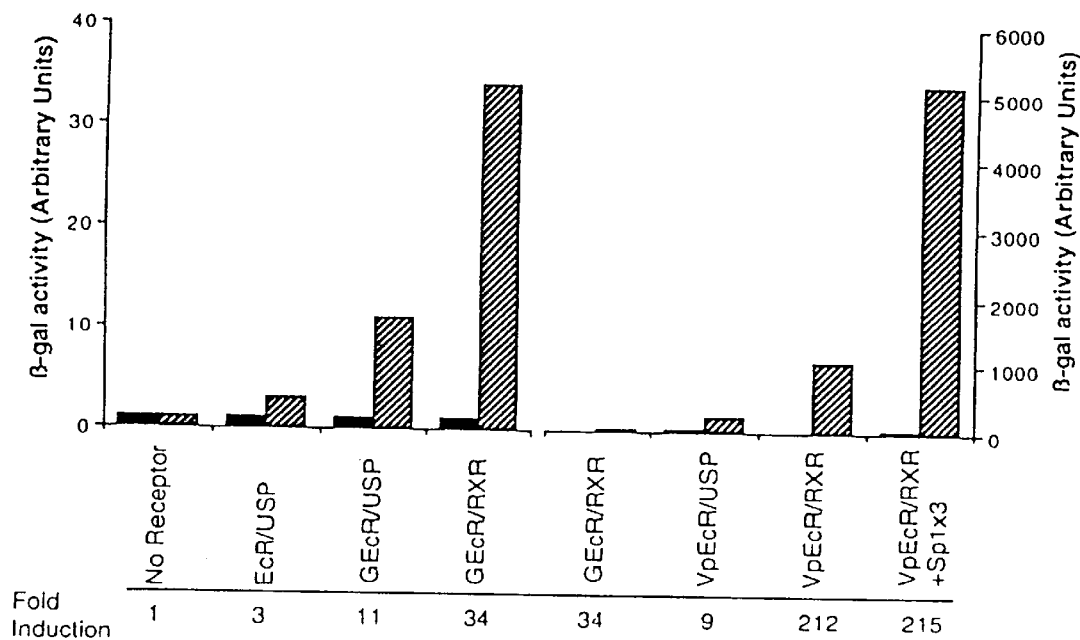
FIGS. 1A–1D show the optimization of ecdysone responsiveness using various combinations of USP or RXR with different modified EcRs.

In accordance with the present invention, there are provided methods for modulating the expression of an exogenous gene in a mammalian subject containing:

(i) a DNA construct comprising said exogenous gene under the control of an ecdysone response element; and (ii) a modified ecdysone receptor which, in the presence of a ligand therefor, and optionally in the further presence of a receptor capable of acting as a silent partner therefor, binds to said ecdysone response element;

said method comprising administering to said subject an effective amount of a ligand for said modified ecdysone receptor; wherein said ligand is not normally present in the cells of said subject; and wherein said ligand is not toxic to said subject.

Thus, in accordance with the present invention the insect molting hormone, ecdysone (as well as analogs and mimics thereof), is advantageously employed as a regulated inducer of gene expression in mammalian systems, i.e., background levels of expression are substantially zero in the absence of conditions required for induction. In a presently preferred aspect of the invention, promoters containing a novel modified ecdysone response element are employed in conjunction with an invention modified ecdysone receptor (preferably having an altered DNA binding specificity) to provide an extremely powerful and specific inducible mammalian expression system. The low basal activity of the invention expression system is advantageously suitable for the expression of transcription factors and toxic genes. The excellent dose response and induction rate characteristics of the invention inducible expression system allow for precise control of both the degree and duration of induction of a desired gene.

Since the invention method provides for regulated gene expression by an exogenous non-mammalian inducer, it can be advantageously employed in a variety of in vivo and in vitro mammalian expression systems. For example, inducible expression of cre recombinase in transgenic mammals, in accordance with invention methods, would enable those of skill in the art to accomplish temporally specific inducible gene targeting of the adult or the developing embryo (O'Gorman et al. (1991) Science 251, 1351–1355).

As employed herein, the terms "modulate" and "modulating" refer to the ability of a given ligand/receptor complex to effect transactivation of transcription of an exogenous gene, relative to such ability of said receptor in the absence of ligand. The actual effect of complex formation on the transactivation activity of a receptor will vary depending on the specific receptor species which are part of the ligand/receptor complex, and on the response element with which the ligand/receptor complex interacts.

As used herein, when referring to genes, the phrase "exogenous to said mammalian subject" or simply "exogenous" refers to any gene wherein the gene product is not naturally expressed in the particular cell where expression is desired. For example, exogenous genes can be either natural or synthetic wild type genes and therapeutic genes, which are introduced into the subject in the form of DNA or RNA. The gene of interest can be introduced into target cells (for in vitro applications), or the gene of interest can be introduced directly into a subject, or indirectly introduced by the transfer of transformed cells into a subject.

"Wild type" genes are those that are native to cells of a particular type. Such genes may be undesirably overexpressed, or may not be expressed in biologically significant levels. Thus, for example, while a synthetic or natural gene coding for human insulin would be exogenous genetic material to a yeast cell (since yeast cells do not naturally contain insulin genes), a human insulin gene inserted into a human skin fibroblast cell would be a wild type gene with respect to that cell since human skin fibroblasts contain genetic material encoding human insulin, although human skin fibroblasts do not express human insulin in biologically significant levels.

Wild type genes contemplated for use in the practice of the present invention include genes which encode a gene product:

the substantial absence of which leads to the occurrence of a non-normal state in said subject; or a substantial excess of which leads to the occurrence of a non-normal state in said subject;

and the like.

As employed herein, the phrase "therapeutic gene" refers to a gene which imparts a beneficial function to the host cell in which such gene is expressed. Therapeutic genes are those that are not naturally found in host cells. For example, a synthetic or natural gene coding for wild type human insulin would be therapeutic when inserted into a skin fibroblast cell so as to be expressed in a human host, where the human host is not otherwise capable of expressing functionally active human insulin in biologically significant levels. In accordance with the methods described herein, therapeutic genes are expressed at a level that provides a therapeutically effective amount of the corresponding therapeutic protein.

Therapeutic genes contemplated for use in the practice of the present invention include genes which encode a gene product:

which is toxic to the cells in which it is expressed; or which imparts a beneficial property to the host subject (e.g., disease resistance, etc);

and the like.

Numerous genomic and cDNA nucleic acid sequences coding for a variety of proteins are well known in the art. Exogenous genetic material useful in the practice of the present invention include genes that encode biologically active proteins of interest, such as, e.g., secretory proteins that can be released from said cell; enzymes that can metabolize a substrate from a toxic substance to a non-toxic substance, or from an inactive substance to a useful substance; regulatory proteins; cell surface receptors; and the like. Useful genes include genes that encode blood clotting factors such as human factors VIII and IX; genes that encode hormones such as insulin, parathyroid hormone, luteinizing hormone releasing factor (LHRH), alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as alpha$_1$-antitrypsin; genes encoding substances that function as drugs, e.g., genes encoding the diphtheria and cholera toxins; and the like.

Typically, nucleic acid sequence information for a desired protein can be located in one of many public access databases, e.g., GENBANK, EMBL, Swiss-Prot, and PIR, or in many biology related journal publications. Thus, those of skill in the art have access to nucleic acid sequence information for virtually all known genes. Those of skill in the art can either obtain the corresponding nucleic acid molecule directly from a public depository or the institution that published the sequence. Optionally, once the nucleic acid sequence encoding a desired protein has been ascertained, the skilled artisan can employ routine methods, e.g., polymerase chain reaction (PCR) amplification, to isolate the desired nucleic acid molecule from the appropriate nucleic acid library. Thus, all known nucleic acids encoding proteins of interest are available for use in the methods and products described herein.

As used herein, the terms "mammal" and "mammalian" refer to humans; domesticated animals, e.g., rats, mice, rabbits, canines, felines, and the like; farm animals, e.g., chickens, bovine, porcine and ovine, and the like; and animals of zoological interest, e.g., monkeys and baboons, and the like.

Modified ecdysone receptors contemplated for use in the practice of the present invention comprise:

a ligand binding domain capable of binding an ecdysteroid;

a DNA-binding domain obtained from a DNA-binding protein; and an activation domain of a transcription factor, wherein at least one of said DNA-binding domain or said activation domain is not obtained from a native ecdysone receptor, with the proviso that when said activation domain is derived from a glucocorticoid receptor, said DNA-binding domain is not derived from a glucocorticoid receptor or an *E. coli* LexA protein. In accordance with the present invention, modified ecdysone receptors function in expression systems, preferably mammalian, to transactivate gene expression from transcription regulatory regions having ecdysone response elements. Preferably, in order to minimize induction of undesired gene expression, modified ecdysone receptors of the invention will have substantially no constitutive activity in mammalian cells.

Ligand binding domains capable of binding an ecdysteroid, as contemplated for use in the preparation of invention modified ecdysone receptors are typically derived from the carboxy-terminal portion of native ecdysone receptor and are able to bind ecdysteroids (Koelle et al., *Cell*, 67:59–77, 1991; and Christopherson et al., *PNAS, USA*, 89:6314–6318, 1992). Ligand binding domains capable of binding an ecdysteroid can be functionally located in either orientation and at various positions within the modified ecdysone receptor of the invention. For example, the ligand binding domain capable of binding an ecdysteroid can be positioned at either the amino or carboxy terminus of the modified receptor, or therebetween. In a preferred embodiment of the present invention, the ligand binding domain capable of binding an ecdysteroid is positioned at the carboxy terminus of the modified receptor (see FIG. 1D).

DNA-binding domains contemplated for use in the preparation of invention modified ecdysone receptors are typically obtained from DNA-binding proteins (e.g., transcription factors). The term "DNA-binding domain" is understood in the art to refer to an amino acid sequence that is able to bind to DNA. As used herein, the term "DNA-binding domain" encompasses a minimal peptide sequence of a DNA-binding protein, up to the entire length of a DNA-binding protein, so long as the DNA-binding domain functions to associate with a particular response element.

Such DNA-binding domains are known to function heterologously in combination with other functional protein domains by maintaining the ability to bind the natural DNA recognition sequence (see, e.g., Brent and Ptashne, 1985, Cell, 43:729–736). For example, hormone receptors are known to have interchangeable DNA-binding domains that function in chimeric proteins (see, e.g., U.S. Pat. No. 4,981,784; and Evans, R., 1988, Science, 240:889–895). Thus, similar to the ligand binding domain of invention modified ecdysone receptor, the DNA-binding domain can be positioned at either the carboxy terminus or the amino terminus, or the DNA-binding domain can be positioned between the ligand binding domain and the activation domain. In preferred embodiments of the present invention, the DNA-binding domain is positioned internally between the ligand binding domain and the activation domain.

"DNA-binding protein(s)" contemplated for use herein belong to the well-known class of proteins that are able to directly bind DNA and facilitate initiation or repression of transcription. Exemplary DNA-binding proteins contemplated for use herein include transcription control proteins (e.g., transcription factors and the like; Conaway and Conaway, 1994, "Transcription Mechanisms and Regulation", Raven Press Series on Molecular and Cellular Biology, Vol. 3, Raven Press, Ltd., New York, N.Y.).

Transcription factors contemplated for use herein as a source of such DNA binding domains include, e.g., homeobox proteins, zinc finger proteins, hormone receptors, helix-turn-helix proteins, helix-loop-helix proteins, basic-Zip proteins (bZip), β-ribbon factors, and the like. See, for example, Harrison, S., "A Structural Taxonomy of DNA-binding Domains," Nature, 353:715–719. Homeobox DNA-binding proteins suitable for use herein include, for example, HOX, STF-1 (Leonard et al., 1993, Mol. Endo., 7:1275–1283), Antp, Mat α-2, INV, and the like. See, also, Scott et al. (1989), Biochem. Biophys. Acta, 989:25–48. It has been found that a fragment of 76 amino acids (corresponding to amino acids 140–215 described in Leonard et al., 1993, Mol. Endo., 7:1275–1283) containing the STF-1 homeodomain binds DNA as tightly as wild-type STF-1. Suitable zinc finger DNA-binding proteins for use herein include Zif268, GLI, XFin, and the like. See also, Klug and Rhodes (1987), Trends Biochem. Sci., 12:464; Jacobs and Michaels (1990), New Biol., 2:583; and Jacobs (1992), EMBO J., 11:4507–4517.

Preferably, the DNA-binding domain used herein is obtained from a member of the steroid/thyroid hormone superfamily of receptors. As used herein, the phrase "member(s) of the steroid/thyroid hormone superfamily of receptors" (also known as "nuclear receptors" or "intracellular receptors") refers to hormone binding proteins that operate as ligand-dependent transcription factors, including identified members of the steroid/thyroid hormone superfamily of receptors for which specific ligands have not yet been identified (referred to hereinafter as "orphan receptors").

Exemplary members of the steroid/thyroid hormone superfamily of receptors (including the various isoforms thereof) include steroid receptors such as glucocorticoid receptor (GR), mineralocorticoid receptor (MR), estrogen receptor (ER), progesterone receptor (PR), androgen receptor (AR), vitamin $D_3$ receptor (VDR), and the like; plus retinoid receptors, such as the various isoforms of retinoic acid receptor (e.g., RARα, RARβ, or RARγ), the various isoforms of retinoid X receptor (e.g., RXRα, RXRβ, or RXRγ), and the like (see, e.g., U.S. Pat. Nos. 4,981,784; 5,171,671; and 5,071,773); thyroid receptors (TR), such as TRα, TRβ, and the like; insect derived receptors such as the ecdysone receptor, and the like; as well as other gene products which, by their structure and properties, are considered to be members of the superfamily, as defined hereinabove, including the various isoforms thereof. Examples of orphan receptors contemplated for use herein as a source of DNA binding domain include HNF4 (see, for example, Sladek et al., in Genes & Development 4: 2353–2365 (1990)), the COUP family of receptors (see, for example, Miyajima et al., in Nucleic Acids Research 16: 11057–11074 (1988), and Wang et al., in Nature 340: 163–166 (1989)), COUP-like receptors and COUP homologs, such as those described by Mlodzik et al., in Cell 60: 211–224 (1990) and Ladias et al., in Science 251: 561–565 (1991), various isoforms of peroxisome proliferator-activated receptors (PPARs; see, for example, Issemann and Green, supra), the insect derived knirps and knirps-related receptors, and the like.

The DNA-binding domains of all members of the steroid/thyroid hormone superfamily of receptors are related, consisting of 66–68 amino acid residues, and possessing about 20 invariant amino acid residues, including nine cysteines. A member of the superfamily can be characterized as a protein which contains these 20 invariant amino acid residues. The highly conserved amino acids of the DNA-binding domain of members of the superfamily are as follows:

```
                                              (SEQ ID NO:1)
Cys - X - X - Cys - X - X - Asp* - X -

Ala* - X - Gly* - X - Tyr* - X - X -

X - X - Cys - X - X - Cys - Lys* - X -

Phe - Phe - X - Arg* - X - X - X - X -

X - X - X - X - X - (X - X -) Cys - X -

X - X - X - X - (X - X - X -) Cys - X -

X - X - Lys - X - X - Arg - X - X -

Cys - X - X - Cys - Arg* - X - X -

Lys* - Cys - X - X - X - Gly* - Met;
``` wherein X designates non-conserved amino acids within the DNA-binding domain; an asterisk denotes the amino acid residues which are almost universally conserved, but for which variations have been found in some identified hormone receptors; and the residues enclosed in parenthesis are optional residues (thus, the DNA-binding domain is a minimum of 66 amino acids in length, but can contain several additional residues).

Modification of existing DNA-binding domains to recognize new target recognition sequences is also contemplated herein. For example, in accordance with the present invention, it has been found that the modification of the "P-box" sequence of DNA-binding domains of members of the steroid/thyroid hormone superfamily of receptors offers unique advantages not present in other chimeric hormone receptors. For example, the modification of a P-box amino acid sequence to preferentially bind to a different hormone response element half-site than the naturally occurring P-box amino acid sequence can reduce undesired background levels of gene expression. Thus, invention receptors and methods provide the advantage of increasing the selectivity of exogenous gene expression in a particular subject.

Figure 2:
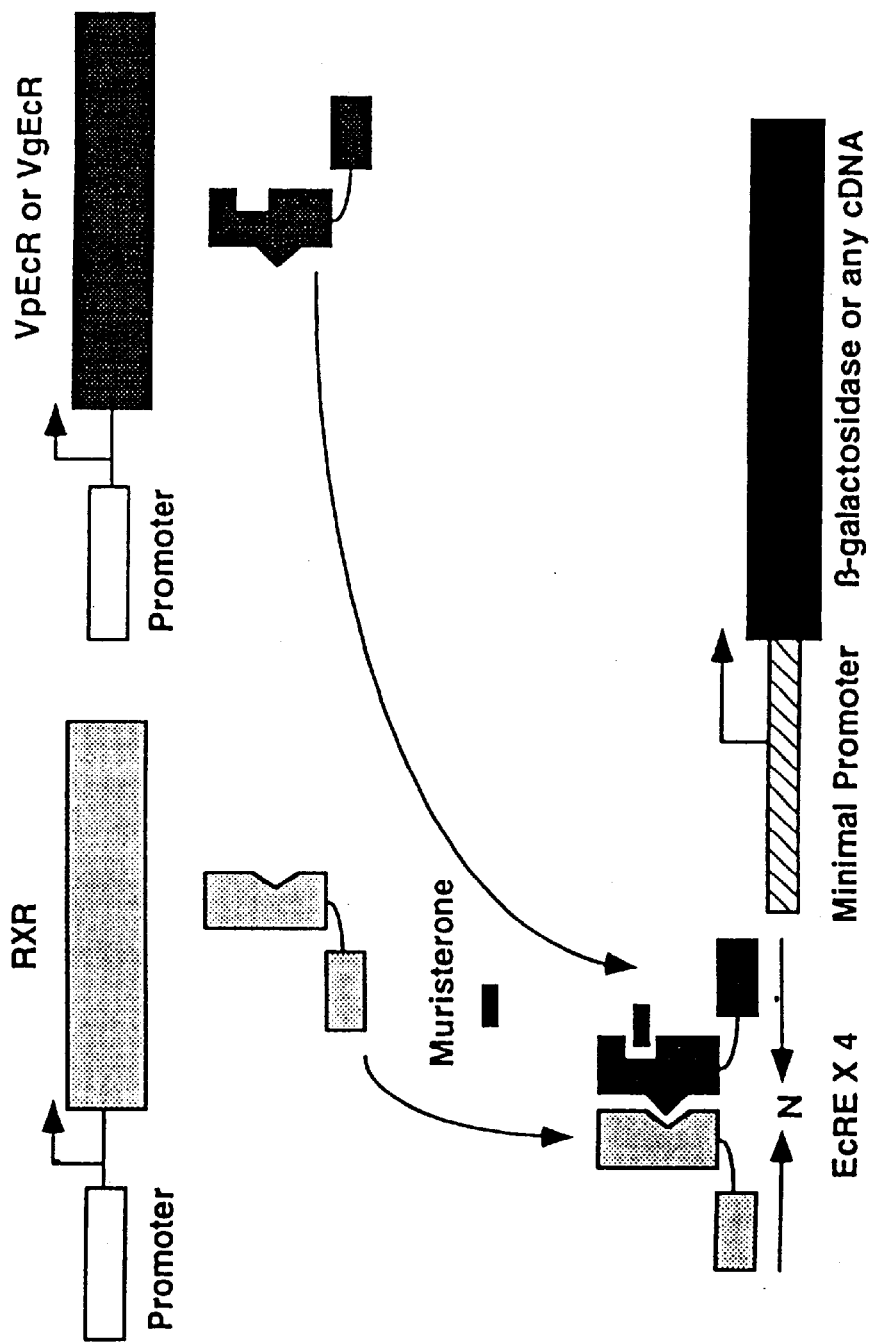
FIG. 2 shows a schematic diagram of an invention ecdysone inducible gene expression system. After expression of RXR and a modified EcR, the two receptors can heterodimerize and transactivate the ecdysone response element-containing promoter in the presence of hormone. The ecdysone response elements are placed upstream of a minimal promoter (i.e., an enhancerless promoter) which can drive the expression of any exogenous cDNA.

As used herein, the phrase "P-box amino acid sequence" refers to the proximal element region in a DNA-binding domain of a hormone receptor that typically occurs at the junction of the first zinc finger and the linker region, e.g., at about amino acids 19–23 of the DNA-binding domain (i.e., amino acids 19–23 of SEQ ID NO:1; see, e.g., Umesono et al. (1989), *Cell*, 57:1139–1146, FIG. 2). Umesono et al. (1989), supra, in Table 1, describe various naturally occurring P-box amino acid sequences for a variety of hormone receptor DNA-binding domains.

In one embodiment of the present invention, the P-box sequence of a hormone receptor DNA-binding domain is modified to have a P-box amino acid sequence that differs from the naturally occurring P-box amino acid sequence. In a preferred embodiment of the present invention, the modified P-box amino acid sequence differs from the naturally occurring P-box amino acid sequence by 3 amino acids.

Preferably, the P-box amino acid sequence is modified so that only the half-site nucleotide sequence recognized by the DNA-binding domain is changed while not altering the spacing between the two half-sites recognized by the DNA-binding domain. For example, when the DNA-binding domain of the ecdysone receptor is employed in an invention modified ecdysone receptor, the P-box can be modified from the amino acid sequence EGCKG (SEQ ID NO:2; which recognizes the half-site —AGGTCA—) to the amino acid sequence GSCKV (SEQ ID NO:3; which recognizes the half-site seqeunce —AGAACA—). In a presently preferred embodiment, when the DNA-binding domain of invention modified ecdysone receptor is derived from ecdysone receptor, the P-box amino acid sequence is modified to GSCKV (SEQ ID NO:3).

It has also been found that in vitro evolution methods can be applied to modify and improve existing DNA-binding domains (see, e.g., Devlin et al., 1990, *Science*, 249:404–406; and Scott and Smith, 1990, *Science*, 249:386–390).

Activation domains contemplated for use in the preparation of invention modified ecdysone receptor are typically derived from transcription factors and comprise a contiguous sequence of amino acids that functions to activate gene expression when associated with a suitable DNA-binding domain and a suitable ligand binding domain. As with the ligand and DNA-binding domains employed for the preparation of invention modified ecdysone receptors, the activation domain can be positioned at the carboxy terminus, the amino terminus or between the ligand binding domain and the DNA binding domain. In preferred embodiments of present invention, the activation domain is positioned at the amino terminus or the carboxy terminus of the modified ecdysone receptor.

Suitable activation domains can be obtained from a variety of sources, e.g., from the N-terminal region of a member of the steroid/thyroid hormone superfamily of receptors, from a transcription factor activation domain, such as, for example, VP16 or GAL4 activation domains, and the like. The presently most preferred activation domain contemplated for use in the practice of the present invention is obtained from the N-terminal region of the VP16 protein.

The presently most preferred modified ecdysone receptors contemplated for use herein are VgEcR (SEQ ID NO:5), VpEcR (SEQ ID NO:7), GEcR (SEQ ID NO:9), Vp16-EcR-B1 or VgEcR-B1, with VgEcR (SEQ ID NO:5) and VgEcR-B1 being especially preferred. The preparation of several of these modified ecdysone receptors is set forth hereinafter in Example 1. See also FIG. 1D. Those modified receptors for which explicit methods of preparation is not provided herein can readily be made using the methodology set forth herein in combination with standard methodology well known to those of skill in the art.

Invention modified ecdysone receptor proteins can be produced by expressing nucleic acid constructs encoding the chimeric proteins in suitable host cells as described in Example 1. Recombinant methods of producing desired proteins by introducing an expression construct into appropriate host cells are well-known in the art. Modified ecdysone receptors of the invention can be introduced into a particular subject by direct introduction of the proteins themselves, by introducing DNA construct(s) encoding the receptor into the subject, or into cells obtained from the subject (wherein the cells are transformed and subsequently returned to the subject).

In a preferred embodiment, invention modified ecdysone receptors are expressed under the control of a tissue specific promoter. As readily understood by those of skill in the art, the term "tissue specific" refers to the substantially exclusive initiation of transcription in the tissue from which a particular promoter drives expression of a given gene.

In accordance with one aspect of the present invention, invention modified ecdysone receptors are present in the form of heterodimeric species comprising an invention modified ecdysone receptor and at least one silent partner of the steroid/thyroid hormone superfamily of receptors. Preferably, the silent partner is a mammalian-derived receptor, with RXR being especially preferred.

Silent partners contemplated herein are members of the steroid/thyroid hormone superfamily of receptors which are capable of forming heterodimeric species with the invention modified ecdysone receptor, wherein the silent partner does not directly participate in binding ligand (i.e., only the modified ecdysone receptor co-partner of the heterodimer binds ligand). The silent partner can either be endogenous to the cells of the subject or can be provided to the subject by introducing DNA construct(s) encoding receptor into the subject. A preferred silent partner for use herein is RXR. In a particular embodiment of the invention methods, exogenous RXR is provided to said mammalian subject.

The formation of heterodimeric receptor(s) can modulate the ability of member(s) of the steroid/thyroid hormone superfamily of receptors to trans-activate transcription of genes maintained under expression control in the presence of ligand for said receptor. For example, formation of a heterodimer of the modified ecdysone receptor with another mammalian hormone receptor promotes the ability of the modified ecdysone receptor to induce trans-activation activity in the presence of an ecdysone response element.

In accordance with another aspect of the present invention, invention modified ecdysone receptors are present in the form of homodimeric species comprising a plurality (i.e., at least two) invention modified ecdysone receptors.

Ligands contemplated for use herein are compounds which, inside a cell, bind to invention modified ecdysone receptors, thereby creating a ligand/receptor complex, which in turn can bind to an appropriate response element. The terms "ecdysone", "ecdysteroid", "ecdysone-analogs", and "ecdysone mimics" as interchangeably used herein, are employed herein in the generic sense (in accordance with common usage in the art), referring to a family of ligands with the appropriate binding and transactivation activity (see, for example, Cherbas et al., in *Biosynthesis, metabolism and mode of action of invertebrate hormones* (ed. J. Hoffmann and M. Porchet), p. 305–322; Springer-Verlag, Berlin). An ecdysone, therefore, is a steroid, steroid-like or non-steroidal compound which acts to modulate gene transcription for a gene maintained under the control of a suitable response element, as described herein.

20-Hydroxy-ecdysone (also known as β-ecdysone) is the major naturally occurring ecdysone. Unsubstituted ecdysone (also known as α-ecdysone) is converted in peripheral tissues to β-ecdysone. Analogs of the naturally occurring ecdysones are also contemplated within the scope of the present invention. Examples of such analogs, commonly referred to as ecdysteroids, include ponasterone A, ponasterone B, ponasterone C, ponasterone D, 26-iodoponasterone A, muristerone A, inokosterone, 26-mesylinokosterone, sidasterone, buterosterone, ajugasterone, makisterone, cyasterone, sengosterone, and the like. Since it has been previously reported that the above-described ecdysones are neither toxic, teratogenic, nor known to affect mammalian physiology, they are ideal candidates for use as inducers in cultured cells and transgenic mammals according to the invention methods.

Additional compounds contemplated for use herein are mimics of the naturally occurring ecdysones, i.e., synthetic organic compounds which have binding and transactivation activities characteristic of the naturally occurring ecdysones. Examples of such compounds, referred to herein as ecdysone mimics, include 1,2-diacyl hydrazines (e.g., those described in U.S. Pat. Nos. 5,424,333 and 5,354,762, the entire contents of each of which are hereby incorporated by reference herein), N'-substituted-N,N'-di-substituted hydrazines (e.g., those described in U.S. Pat. No. 5,117,057, the entire contents of which are hereby incorporated by reference herein), dibenzoylalkyl cyanohydrazines (e.g., those described in European Application No. 461,809, the entire contents of which are hereby incorporated by reference herein), N-substituted-N-alkyl-N,N'-diaroyl hydrazines (e.g., those described in U.S. Pat. No. 5,225,443, the entire contents of which are hereby incorporated by reference herein), N-substituted-N-acyl-N-alkyl, carbonyl hydrazines (e.g., those described in European Application No. 234,944, the entire contents of which are hereby incorporated by reference herein), N-aroyl-N'-alkyl-N'-aroyl hydrazines (e.g., those described in U.S. Pat. No. 4,985,461, the entire contents of which are hereby incorporated by reference herein), and the like. Compounds of specific interest are those having the formula:

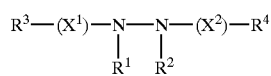

wherein:

$R^1$ is optionally hydrogen, lower alkyl or substituted lower alkyl, alkenyl or substituted alkenyl, alkynyl or substituted alkynyl, aryl or substituted aryl, heteroaryl or substituted heteroaryl, and the like. $R^1$ is not present when $X^1$ is part of a carbon-nitrogen double bond linking $R^3$ to the hydrazino group.

$R^2$ is optionally hydrogen, alkyl or substituted alkyl, cyclohexyl or substituted cyclohexyl, and the like. $R^2$ is not present when $X^2$ is part of a carbon-nitrogen double bond linking $R^4$ to the hydrazino group.

$R^3$ and $R^4$ are independently part of an appropriately substituted carbon-nitrogen double bond which links $R^3$ and/or $R^4$ to the hydrazino linkage, or $R^3$ and $R^4$ are independently aryl or substituted aryl, heteroaryl or substituted heteroaryl, provided, however, that when two adjacent positions on the aryl or heteroaryl moieties are substituted with alkoxy, thioalkyl, alkylamino, or dialkylamino groups, these groups may be joined to form a 5- or 6-membered heterocyclic ring system, or $R^3$ and $R^4$ are independently heterocyclic or substituted heterocyclic, cycloalkyl or substituted cycloalkyl, and the like.

$X^1$ and $X^2$ are independently —C(O)—, —C(S)—, —C(NR$_2$)—, —C(=CN)NH—, —C(O)O—, —C(O)NH—, —C(O)NHSO$_2$—, —CH$_2$—, —SO$_2$—, —P(O)CH$_3$—, and the like, as well as an appropriate substituted carbon-nitrogen double bond which links $R^3$ and/or $R^4$ to the hydrazino linkage.

As employed herein, "alkyl" refers to alkyl groups having in the range of 1 up to 8 carbon atoms; "lower alkyl" refers to alkyl groups having in the range of 1 up to 4 carbon atoms; and "substituted alkyl" or "substituted lower alkyl", comprises alkyl (or lower alkyl) groups further bearing one or more substituents selected from halogen, cyano, nitro, hydroxy, alkoxy (—OR), thioalkyl (—SR), —NR$_2$, —NRC(O)R, —OC(O)R, —C(O)OR, —C(O)NR$_2$, —C(O)R, wherein each R is independently hydrogen or lower alkyl, and the like.

As employed herein, "cycloalkyl" refers to cyclic ring-containing groups containing in the range of about 5 up to 8 carbon atoms, and "substituted cycloalkyl" refers to cycloalkyl groups further bearing one or more substituents as set forth above, as well as lower alkyl.

As employed herein, "heterocyclic" refers to cyclic (i.e., ring-containing) groups containing one or more (up to four) heteroatoms (e.g., N, O, S, or the like) as part of the ring structure, and having in the range of 2 up to 5 nuclear carbon atoms and "substituted heterocyclic" refers to heterocyclic groups further bearing one or more substituents as set forth above, as well as lower alkyl.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above, as well as lower alkyl.

As employed herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

Presently preferred ecdysone mimics contemplated for use herein include compounds wherein $R^1$ is hydrogen; $R^2$ is an alkyl group possessing considerable bulk (such as, for example, alkyl groups containing a tertiary carbon center, e.g., —$C(R'')_3$, wherein each R" is methyl or greater). Examples of alkyl groups having sufficient bulk for use herein include tert-butyl, sec-butyl, isopropyl, isobutyl, cyclohexyl, cyclopentyl, dicyclopropylmethyl, (cyclohexyl) ethyl, and the like); $X^1$ and $X^2$ are both —C(O)—; $R^3$ is phenyl, substituted phenyl (with hydroxy, alkoxy, halo and/or substituted amino substituents being preferred, with 3,4-disubstitution pattern being especially preferred), heterocyclic (e.g., pyridyl or pyrimidine) or substituted heterocyclic (with halo, alkyl, thioalkyl, hydroxy, alkoxy, and/or amino substituents being preferred); and $R^4$ is phenyl or substituted phenyl, heteroaryl or substituted heteroaryl or a bulky alkyl or cycloalkyl group.

Especially preferred ecdysone mimics contemplated for use herein include N'-(3,5-dimethylbenzoyl)-N-(4-ethylbenzoyl)-N'-(tert-butyl) hydrazine, N,N'-dibenzoyl-N'-(tert-butyl) hydrazine, N'-(3,5-dimethylbenzoyl)-N-(4-ethylbenzyl)-N'-(tert-butyl) hydrazine, N'-(3,5-dimethylbenzoyl)-N-(2-methyl-3,4-(ethylenedioxy)-benzoyl)-N'-(tert-butyl) hydrazine, 3,5-di-tert-butyl-4-hydroxy-N-isobutyl-benzamide, 8-O-acetylharpagide, and the like.

Ligands contemplated for use in the practice of the present invention are characterized as not normally being present in the cells of the subject, meaning that the ligand is exogenous to the subject. Ecdysteroids, for example, are not naturally present in mammalian systems. Thus, in accordance with the invention method, unless and until an ecdysteroid is administered to the subject, substantially no expression of the desired gene occurs.

An effective amount of ligand contemplated for use in the practice of the present invention is the amount of ligand (i.e., ecdysteroid) required to achieve the desired level of gene expression product. Ligand can be administered in a variety of ways, as are well-known in the art. For example, such ligands can be administered topically, orally, intravenously, intraperitoneally, intravascularly, and the like.

As readily recognized by those of skill in the art, it may be desirable to be able to rapidly induce or rapidly turn off expression by the invention expression system. This can readily be accomplished by administration of a suitable ecdysone antagonist before or after induction of the system (e.g., to prevent undesired activation of the system, to promote rapid induction, to rapidly terminate expression, and the like). Numerous ecdysone antagonists are known in the art, e.g., ajugalactone.

In accordance with a particular embodiment of the present invention, pharmaceutically acceptable formulations, and kits thereof, comprising at least one ecdysteroid, and a pharmaceutically acceptable carrier are contemplated. In accordance with another aspect of the present invention, pharmaceutically acceptable formulations consisting essentially of at least one ecdysteroid and a pharmaceutically acceptable carrier, are contemplated. Pharmaceutical formulations of the present invention can be used in the form of a solid, a solution, an emulsion, a dispersion, a micelle, a liposome, and the like, wherein the resulting formulation contains one or more of the ecdysteroids of the present invention, as an active ingredient, in admixture with an organic or inorganic carrier or excipient suitable for enteral or parenteral applications.

The active ingredient may be compounded, for example, with the usual non-toxic, pharmaceutically acceptable carriers suitable for oral, topical, nasal, transdermal, intravenous, subcutaneous, intramuscular, intracutaneous, intraperitoneally, intravascular and the like administration. Administration in the form of creams, lotions, tablets, dispersible powders, granules, syrups, elixirs, sterile aqueous or non-aqueous solutions, suspensions or emulsions, and the like, is contemplated. Exemplary pharmaceutically acceptable carriers include carriers for tablets, pellets, capsules, suppositories, solutions, emulsions, suspensions, and any other form suitable for use. Such carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound (i.e., ecdysteroid as described herein) is included in the pharmaceutically acceptable formulation in an amount sufficient to produce the desired effect upon the process or condition of diseases.

Pharmaceutically acceptable formulations containing the active ingredient may be in a form suitable for oral use, for example, as aqueous or oily suspensions, syrups or elixirs, tablets, troches, lozenges, dispersible powders or granules, emulsions, or hard or soft capsules. For the preparation of oral liquids, suitable carriers include emulsions, solutions, suspensions, syrups, and the like, optionally containing additives such as wetting agents, emulsifying and suspending agents, dispersing agents, sweetening, flavoring, coloring, preserving and perfuming agents, and the like. Formulations intended for oral use may be prepared according to any method known to the art for the manufacture of pharmaceutically acceptable formulations.

Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutically acceptable formulations may be in the form of a sterile injectable suspension. Suitable carriers include non-toxic parenterally-acceptable sterile aqueous or non-aqueous solutions, suspensions, or emulsions. This suspension may be formulated according to known methods using suitable dispersing or wetting agents and suspending agents. They can also be manufactured in the form of sterile water, or some other sterile injectable medium immediately before use. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. They may be sterilized, for example, by filtration through a bacteria-retaining filter, by incorporating sterilizing agents into the formulations, by irradiating the formulations, or by heating the formulations. Sterile injectable suspensions may also contain adjuvants such as preserving, wetting, emulsifying, and dispersing agents. Buffers, preservatives, antioxidants, and the like can be incorporated as required.

Compounds contemplated for use in the practice of the present invention may also be administered in the form of suppositories for rectal administration of the drug. These formulations may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The pharmaceutically acceptable formulations are administered in a manner compatible with the route of administration, the dosage formulation, and in a therapeutically effective amount. The required dosage will vary with the particular treatment desired, the degree and duration of therapeutic effect desired, the judgment of the practitioner, as well as properties peculiar to each individual. Moreover, suitable dosage ranges for systemic application depend on the route of administration. It is anticipated that dosages between about 10 micrograms and about 1 milligram per kilogram of body weight per day will be used for therapeutic treatment.

An effective amount of the pharmaceutically acceptable formulation contemplated for use in the practice of the present invention is the amount of the pharmaceutically acceptable formulation (e.g., ecdysteroids(s)) required to achieve the desired level of transcription and/or translation of exogenous nucleic acid. A therapeutically effective amount is typically an amount of a ligand or ligand precursor that, when administered in a pharamceutically acceptable formulation, is sufficient to achieve a plasma concentration of the transcribed or expressed nucleic acid product from about 0.1 µg/ml to about 100 µg/ml, preferably from about 1.0 µg/ml to about 50 µg/ml, more preferably at least about 2 µg/ml and usually 5 to 10 µg/ml.

Pharmaceutically acceptable formulations containing suitable ligand(s) are preferably administered intravenously, as by injection of a unit dose, for example.

The term "unit dose," when used in reference to a pharmaceutically acceptable formulation of the present invention, refers to a quantity of the pharmaceutical formulation suitable as unitary dosage for the subject, each unit containing a predetermined quantity of active material calculated to produce the desired therapeutic effect in association with the required diluent, i.e., carrier, or vehicle. It may be particularly advantageous to administer such formulations in depot or long-lasting form as discussed hereinafter.

Suitable regimes for initial administration and booster shots are variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Ecdysone response elements contemplated for use in the practice of the present invention (relating to modulation of the expression of exogenous genes in a subject) include native, as well as modified ecdysone response elements. Since invention modified ecdysone receptors can function as either homodimers or as heterodimers (with a silent partner therefor), any response element that is responsive to an invention modified ecdysone receptor, in the form of a homodimer or heterodimer, is contemplated for use in the invention methods described herein. As is readily recognized by those of skill in the art, modified receptors according to the invention (whether in the form of a homodimer or a heterodimer) can bind to either a response element having an inverted repeat motif (i.e., two or more half sites in mirror image orientation with respect to one another), or to a response element having a direct repeat motif.

In a preferred embodiment of the invention, invention modified ecdysone response elements are engineered so as to no longer be capable of binding to a farnesoid hormone receptor (since the mammalian farnesoid hormone receptor is able to bind to native ecdysone receptor response element). Invention modified ecdysone response elements provide low background expression levels of the exogenous gene and increase the selectivity of the gene expression system when used in mammalian systems.

Ecdysone response elements contemplated for use herein are short cis-acting sequences (i.e., having about 12–20 bp) that are required for activation of transcription in response to a suitable ligand, such as ecdysone or muristerone A, associated with a particular hormone receptor. The association of these response elements with otherwise ecdysone-nonresponsive regulatory sequences causes such regulatory sequences to become ecdysone responsive. Ecdysone response element sequences function in a position- and orientation-independent fashion.

The native ecdysone response element has been previously described, see, e.g., Yao et al., *Cell*, 71:63–72, 1992. Modified ecdysone response elements according to present invention comprise two half-sites (in either direct repeat or inverted repeat orientation to one another), separated by a spacer of 0–5 nucleotides. As used herein, the term "half-site" refers to a contiguous 6 nucleotide sequence that is bound by a particular member of the steroid/thyroid hormone superfamily of receptors. Each half-site is typically separated by a spacer of 0 up to about 5 nucleotides. Typically, two half-sites with a corresponding spacer make up a hormone response element. Hormone response elements can be incorporated in multiple copies into various transcription regulatory regions.

Preferred modified ecdysone response elements according to the invention comprise, in any order, a first half-site and a second half-site separated by a spacer of 0–5 nucleotides;
  wherein the first and second half-sites are inverted with respect to each other;
  wherein said first half-site has the sequence:

—RGBNNM—, (or complements thereof) wherein
  each R is independently selected from A or G;
  each B is independently selected from G, C, or T;
  each N is independently selected from A, T, C, or G; and
  each M is independently selected from A or C;
with the proviso that at least 4 nucleotides of each —RGBNNM— group of nucleotides are identical with the nucleotides at comparable positions of the sequence —AGGTCA—; and
  said second half-site is obtained from a glucocorticoid receptor subfamily response element.

The complement to the -RGBNNM- sequence set forth above is:

—YCVNNK—, wherein
each Y is independently selected from T or C;
each V is independently selected from C, G, or A;
each N is independently selected from A, T, C, or G; and
each K is independently selected from T or G.

Exemplary first half-sites having the —RGBNNM— motif for use in the invention modified ecdysone response element include, for example, half-sites selected from —AGGGCA—, —AGTTCA—, —AGGTAA—, —AGGTCA—, —GGTTCA—, —GGGTTA—, —GGGTGA—, —AGGTGA—, or —GGGTCA—. A particularly preferred first half-site is —AGTGCA—.

Glucocorticoid receptor subfamily response elements contemplated for use in the practice of the present invention are response elements having half-sites that are typically bound by glucocorticoid, mineralocorticoid, progesterone or androgen receptors. Suitable half-sites from glucocorticoid receptor subfamily response elements can be selected from the following sequence (in either orientation):

—RGNNCA—

(or complements thereof such as —YCNNGT—), wherein R, Y and N are as defined above. Exemplary half-sites having the —RGNNCA—motif for use in the invention modified ecdysone response element include —AGAACA—, —GGAACA—, —AGTTCA—, —AGGTCA—, —GGAACA—, —GGTTCA—, —GGGTCA—, —GGGTCA—, —AGGTGA—, —GGGTCA—, and the like, as well as complements thereof. Particularly preferred half-sites having the —RGNNCA—motif include —AGAACA—and —GGAACA—, with —AGAACA—being especially preferred.

When the above-described modified ecdysone response elements are employed to bind invention heterodimeric receptors, the second half-site is inverted with respect to the first half-site. For example, when describing a single-strand of an invention modified ecdysone response element in the 5'-3' direction, the following general motif can be employed:

RGBNNM—(N)$_x$—TGNNCY (SEQ ID NO:10), where x is an integer of 0 up to about 5, with x=1 being especially preferred. As an alternative orientation to the above described response element motif (SEQ ID NO:10), an invention response element can be described in the 5'-3' direction as:

RGNNCA—(N)$_x$—KNNVCY (SEQ ID NO:11), where x is an integer of 0 up to about 5, with x=1 being especially preferred.

In preferred embodiments of the present invention, the first half-site is obtained from an ecdysone response element and the second half-site is obtained from a hormone response element selected from a glucocorticoid response element, a mineralocorticoid response element, a progesterone response element or an androgen response element. In a particularly preferred embodiment of the present invention, the first half-site is obtained from an ecdysone response element and the second half-site is obtained from a glucocorticoid response element.

In a particularly preferred embodiment of the invention modified ecdysone response element, the first half-site is AGTGCA and said second half-site is TGTTCT. The presently most preferred modified-ecdysone response element for use in the invention methods is:

AGTGCA—N—TGTTCT (SEQ ID NO:12).

In another aspect of the invention, when modified ecdysone receptors of the invention exist as homodimers, response elements employed preferably have a direct repeat motif (instead of the above-described inverted repeat motif), as follows:

RGBNNM—(N)$_{x'}$—RGBNNM (SEQ ID NO:13), where R, B, N and M are as previously defined, and x' is an integer of 0 up to about 5, with x'=3 being especially preferred.

Invention modified ecdysone response elements are characterized as having substantially no constitutive activity, which refers to the substantial absence of background levels of gene expression initiated by invention modified ecdysone response elements when introduced into mammalian expression systems. Since it has been found that mammalian farnesoid hormone receptors are able to bind to and transactivate gene expression from native ecdysone response elements, in certain embodiments of the present invention (e.g., where it is desired to avoid farnesoid-mediated background expression), modified ecdysone response elements are employed.

Presently preferred invention modified ecdysone response elements are further characterized as having substantially no binding affinity for farnesoid X receptor (FXR), i.e., invention response elements are incapable of binding FXR (which would thereby create undesired background levels of expression). Thus, presently preferred invention modified ecdysone response elements preferably induce basal levels of expression of substantially zero.

Response elements employed in the practice of the present invention are operably linked to a suitable promoter for expression of exogenous gene product(s). As used herein, the term "promoter" refers to a specific nucleotide sequence recognized by RNA polymerase, the enzyme that initiates RNA synthesis. This sequence is the site at which transcription can be specifically initiated under proper conditions. When exogenous genes, operatively linked to a suitable promoter, are introduced into the cells of a suitable host, expression of the exogenous genes is controlled by the presence of ecdysteroid compounds, which are not normally present in the host cells.

In accordance with another embodiment of the present invention, there are provided methods of inducing the expression of an exogenous gene in a mammalian subject containing:

(i) a DNA construct comprising an exogenous gene under the control of an ecdysone response element,
(ii) DNA encoding a modified ecdysone receptor under the control of an inducible promoter; wherein said modified ecdysone receptor, in the presence of a ligand therefor, and optionally in the further presence of a receptor capable of acting as a silent partner therefor, binds to said ecdysone response element, and
(iii) a ligand for said modified ecdysone receptor;

said method comprising subjecting said subject to conditions suitable to induce expression of said modified ecdysone receptor.

Inducible promoters contemplated for use in the practice of the present invention are transcription regulatory regions that do not function to transcribe mRNA unless inducing conditions are present. Examples of suitable inducible promoters include DNA sequences corresponding to: the *E. coli* lac operator responsive to IPTG (see Nakamura et al., *Cell*, 18:1109–1117, 1979); the metallothionein promoter metal-regulatory-elements responsive to heavy-metal (e.g. zinc) induction (see Evans et. al, U.S. Pat. No. 4,870,009), the phage T71ac promoter responsive to IPTG (see Studier et al., *Meth. Enzymol.*, 185: 60–89, 1990; and U.S. Pat. No. 4,952,496), the heat-shock promoter, and the like.

In accordance with another embodiment of the present invention, there are provided methods of inducing expression of an exogenous gene in a mammalian subject containing a DNA construct comprising said exogenous gene under the control of an ecdysone response element, said method comprising introducing into said subject:

a modified ecdysone receptor; and a ligand for said modified ecdysone receptor, wherein said receptor, in combination with a ligand therefor, and optionally in the further presence of a receptor capable of acting as a silent partner therefor, binds to said ecdysone response element, activating transcription therefrom.

In accordance with another embodiment of the present invention, there are provided methods for the expression of recombinant products detrimental to a host organism, said method comprising:

transforming suitable host cells with:
  (i) a DNA construct encoding said recombinant product under the control of an ecdysone response element, and
  (ii) DNA encoding a modified ecdysone receptor;

growing said host cells in suitable media; and inducing expression of said recombinant product by introducing into said host cells ligand(s) for said modified ecdysone receptor, and optionally a receptor capable of acting as a silent partner for said modified ecdysone receptor.

Recombinant products detrimental to a host organism contemplated for expression in accordance with the present invention include any gene product that functions to confer a toxic effect on the organism. For example, inducible expression of a toxin such as the diptheroid toxin would allow for inducible tissue specific ablation (Ross et al. (1993) *Genes and Development* 7, 1318–1324). Thus, the numerous gene products that are known to induce apoptosis in cells expressing such products are contemplated for use herein (see, e.g, *Apoptosis, The Molecular Basis of Cell Death*, Current Communications In Cell & Molecular Biology, Cold Spring Harbor Laboratory Press, 1991).

Suitable media contemplated for use in the practice of the present invention include any growth and/or maintenance media, in the substantial absence of ligand(s) which, in combination with an invention modified ecdysone receptor, is(are) capable of binding to an ecdysone response element.

In accordance with another embodiment of the present invention, there are provided gene transfer vectors useful for the introduction of invention constructs into suitable host cells. Such gene transfer vectors comprise a transcription regulatory region having a minimal promoter (i.e., a promoter region that does not have an enhancer), and an invention modified ecdysone response element, wherein said regulatory region is operatively associated with DNA containing an exogenous gene, and wherein said modified ecdysone response element is present in multiple copies. The number of copies of response elements can readily be varied by those of skill in the art. For example, transcription regulatory regions can contain from 1 up to about 50 copies of a particular response element, preferably 2 up to about 25 copies, more preferably 3 up to about 10–15 copies, with about 4–6 copies being especially preferred.

Gene transfer vectors (also referred to as "expression vectors") contemplated for use herein are recombinant nucleic acid molecules that are used to transport exogenous nucleic acid into cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted DNA.

As used herein, the phrase "transcription regulatory region" refers to the region of a gene or expression construct that controls the initiation of mRNA transcription. Regulatory regions contemplated for use herein typically comprise at least a minimal promoter in combination with an ecdysone response element. A minimal promoter, when combined with an enhancer region (e.g., a hormone response element), functions to initiate mRNA transcription in response to a ligand/receptor complex. However, transcription will not occur unless the required inducer (ligand) is present.

As used herein, the phrase "operatively associated with" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to and transcribes the DNA.

Preferably, the transcription regulatory region further comprises a binding site for an ubiquitous transcription factor. Such a binding site is preferably positioned between the promoter and modified ecdysone response element of the invention. Suitable ubiquitous transcription factors for use herein are well-known in the art and include, for example, Sp1.

Expression vectors suitable for use in the practice of the present invention are well known to those of skill in the art and include those that are replicable in eukaryotic cells and/or prokaryotic cells as well as those that remain episomal and those that integrate into the host cell genome. Expression vectors typically further contain other functionally important nucleic acid sequences, such as expression constructs encoding antibiotic resistance proteins, and the like.

Exemplary eukaryotic expression vectors include eukaryotic constructs, such as the pSV-2 gpt system (Mulligan et al., *Nature*, 1979, 277:108–114); pBlueSkript (Stratagene, La Jolla, Calif.), the expression cloning vector described by Genetics Institute (*Science*, 1985, 228:810–815), and the like. Each of these plasmid vectors are capable of promoting expression of the invention chimeric protein of interest.

Promoters, depending upon the nature of the regulation, may be constitutively or inducibly regulated, or may be tissue-specific (e.g., expressed only in T-cells, endothelial cels, smooth muscle cells, and the like). Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, elongation factor 1α (EF1α) promoter, albumin promoter, APO A1 promoter, cyclic AMP dependent kinase II (CaMKII) promoter, keratin promoter, CD3 promoter, immunoglobulin light or heavy chain promoters, neurofiliment promoter, neuron specific enolase promoter, L7 promoter, CD2 promoter, myosin light chain kinase promoter, HOX gene promoter, thymidine kinase (TK) promoter, RNA Pol II promoter, MYOD promoter, MYF5 promoter, phophoglycerokinase (PGK) promoter, Stf1 promoter, Low Density Lipoprotein (LDL) promoter, and the like.

Suitable means for introducing (transducing) expression vectors containing nucleic acid constructs according to the invention into host cells to produce transduced recombinant cells (i.e., cells containing recombinant heterologous nucleic acid) are well-known in the art (see, for review, Friedmann, 1989, Science, 244:1275–1281; Mulligan, 1993, Science, 260:926–932, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extrachromosomal (i.e., episomal) maintenance, or the heterologous nucleic acid can be donor nucleic acid that integrates into the genome of the host.

In a specific embodiment, said gene transfer vector is a viral vector, preferably a retroviral vector. Retroviral vectors are gene transfer plasmids that have an expression construct encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, mouse mammary tumor virus vectors (e.g., Shackleford et al., 1988, *PNAS, USA*, 85:9655–9659), and the like.

Various procedures are also well-known in the art for providing helper cells which produce retroviral vector particles which are essentially free of replicating virus. See, for example, U.S. Pat. No. 4,650,764; Miller, *Human Gene Therapy*, 1:5–14 (1990); Markowitz, et al., *Journal of Virology*, 61(4):1120–1124 (1988); Watanabe, et al., *Molecular and Cellular Biology*, 3(12):2241–2249 (1983); Danos, et al., *Proc. Natl. Acad. Sci.*, 85:6460–6464 (1988); and Bosselman, et al., *Molecular and Cellular Biology*, 7(5):1797–1806 (1987), which disclose procedures for producing viral vectors and helper cells which minimize the chances for producing a viral vector which includes a replicating virus.

Recombinant retroviruses suitable for carrying out the invention methods are produced employing well-known methods for producing retroviral virions. See, for example, U.S. Pat. No. 4,650,764; Miller, *Human Gene Therapy*, 1:5–14 (1990); Markowitz, et al., *Journal of Virology*, 61(4):1120–1124 (1988); Watanabe, et al., *Molecular and Cellular Biology*, 3(12):2241–2249 (1983); Danos, et al., *Proc. Natl. Acad. Sci.*, 85:6460–6464 (1988); and Bosselman, et al., *Molecular and Cellular Biology*, 7(5):1797–1806 (1987).

In accordance with another embodiment of the present invention, there are provided recombinant cells containing a nucleic acid encoding modified ecdysone receptor(s) according to the invention. Exemplary eukaryotic cells for introducing expression vectors according to the invention include, e.g., CV-1 cells, P19 cells and NT2/D1 cells (which are derived from human embryo carcinomas), COS cells, mouse L cells, Chinese hamster ovary (CHO) cells, primary human fibroblast cells, human embryonic kidney cells, African green monkey cells, HEK 293 (ATCC accession #CRL 1573; U.S. Pat. No. 5,024,939), Ltk$^-$ cells (ATCC accession #CCL1.3), COS-7 cells (ATCC under accession #CRL 1651), DG44 cells (dhfr$^-$ CHO cells; see, e.g., Urlaub et al. (1986) Cell. Molec. Genet. 12: 555), cultured primary tissues, cultured tumor cells, and the like. Presently preferred cells include CV-1 and 293 cells.

In accordance with another embodiment of the present invention, there is provided a transgenic mammal containing a nucleic acid encoding an invention modified ecdysone receptor. As used herein, the phrase "transgenic mammal" refers to a mammal that contains one or more inheritable expression constructs containing a recombinant modified ecdysone receptor transgene and/or an exogenous gene under the transcription control of an invention modified ecdysone response element. Preferably, an invention transgenic mammal also contains one or more inheritable expression constructs containing a member of the steroid/thyroid hormone superfamily of receptors that functions as a silent partner for modified ecdysone receptor (e.g., RXR).

Methods of making transgenic mammals using a particular nucleic acid construct are well-known in the art. When preparing invention transgenic animals, it is preferred that two transgenic lines are generated. The first line will express, for example, RXR and a modified EcR (e.g., VpEcR). Tissue specificity is conferred by the selection of tissue-specific promoters (e.g., T-cell specific) that will then direct the expression of the receptors. A second line contains an ecdysone responsive promoter controlling the expression of an exogenous cDNA.

In a preferred embodiment of the present invention, an invention transgenic mammal contains one or more expression constructs containing nucleic acid encoding a modified ecdysone receptor, exogenous RXR, and an exogenous gene under the transcription control of an invention modified ecdysone response element. It has been found that in transgenic mice containing an ecdysone inducible promoter (i.e., an invention modified ecdysone response element) and expressing a modified ecdysone receptor and RXR, muristerone treatment can activate gene expression. Thus, with tissue specific expression of the modified ecdysone receptor and RXR and timely hormone treatment, inducible gene expression can be achieved with spatial, dosage, and temporal specificity.

In accordance with another embodiment of the present invention, there are provided methods for inducing expression of an exogenous gene in a transgenic mammal containing a modified ecdysone receptor according to the invention, said method comprising:

introducing into said mammal a DNA construct encoding an exogenous gene under the transcription control of an ecdysone response element responsive to said modified ecdysone receptor; and administering to said mammal an amount of ligand for said modified ecdysone receptor effective to induce expression of said exogenous gene.

As discussed hereinbefore, the modified ecdysone receptor forms a homodimer, or optionally a heterodimer in the presence of a silent partner of the steroid/thyroid hormone superfamily of receptors, and functions to activate transcription from an expression vector having a response element responsive to the particular homodimer or heterodimer formed.

In accordance with another embodiment of the present invention, there are provided methods for the induction of two different genes in a mammalian subject comprising: activating a first exogenous gene employing the invention ecdysone inducible system; and activating a second gene using a tetracycline inducible system. The invention method for inducing two different genes is particularly advantagous because it permits the temporal, spatial, and dosage specific control of two exogenous genes.

The tetracycline inducible system is well-known in the art (see, e.g., Gossen et al. (1992) Proc. Natl. Acad. Sci. 89, 5547–5551; Gossen et al.(1993) TIBS 18, 471–475; Furth et al. (1994) Proc. Natl. Acad. Sci. 91, 9302–9306; and Shockett et al. (1995) Proc. Natl. Acad. Sci. 92, 6522–6526).

All U.S. and Foreign Patent publications, textbooks, and journal publications referred to herein are hereby expressly incorporated by reference in their entirety. The invention will now be described in greater detail by reference to the following non-limiting examples.

EXAMPLE 1

Preparation of Modified Ecdysone Receptors
Plasmid Preparation

The plasmids CMX-EcR, CMX-USP, CMX-FXR, CMX-hRXRa, EcREx5-ΔMTV-Luc, CMX-GEcR, MMTV-luc, and CMX-GR have been previously described (Yao, et al., Nature 366:476–479 (1993) and Forman, et al. Cell 81:687–693 (1995)).

The plasmid CMX-VpEcR was constructed by ligation of an EcoRI fragment of psk-EcR and CMX-Vp16.

The plasmid CMX-VgEcR was generated by site-directed mutagenesis of CMX-VpEcR using the Transformer Mutagenesis Kit (Clontech) and the mutagenic Oligonucleotide (SEQ ID NO:14):

```
5'-TACAACGCCCTCACCTGTGGATCCTGCAAGGTGTTTCTTTCGACGCAGC-3'.
```

Mutagenesis of VpEcR to VgEcR altered the P-box region of the DNA binding domain of ecdysone receptor to resemble that of GR (Umesono and Evans, Cell 57:1139–1146 (1989)). The following amino acids in the DNA-binding domain of the ecdysone receptor were altered: E282G, G283S, and G286V (E=glutamate, G=glycine, S=serine, V=valine).

The reporter construct EcREx4-ΔHSP-β-gal was constructed by oligomerizing two annealed oligonucleotides containing the HSP-EcRE (Yao, et al., Nature 366:476–479 (1993)).

EcREx4-Sp1x3-ΔHSP-βgal was constructed by ligating the following annealed oligonucleotides into the Asp718 site of EcREx4-HSP-β-gal (SEQ ID NO:15):

```
5'-GTACTCCCGGGGCGGGGCTATGCGGGGCGGGGCTAATCGCTAGGGGCGGCGCA-3'   and (SEQ ID NO:16):

5'-GTACTGCCCCGCCCCTAGCGATTAGCCCCGCCCCGCATAGCCCCGCCCCGGGA-3'.
```

ΔHSP is a minimal promoter derived from the Drosophila heat shock promoter with its enhancers deleted.

To generate the construct E/GREx4-ΔMTV-Luc, the following oligonucleotides (SEQ ID NO:17):

```
5'-AGCTCGATGGACAAGTGCATTGTTCTTTGCTGAA-3';   and (SEQ ID NO:18):

5'-AGCTTTCAGCAAGAGAACAATGCACTTGTCCATCG-3',
``` were annealed, multimerized, and ligated into the HindIII site of ΔMTV-Luc. The resulting reporter contained 4 copies of the invention modified ecdysone response element E/GRE.

To produce the plasmid pRC-ESHβ, a BglII/(XhoI) fragment containing EcREx4-Sp1x3-ΔHSP-β-gal was subcloned into BglII/(NotI) digested pRC-CMV (Invitrogen, San Diego, Calif.), which contains a neomycin resistance gene.

Cell Culture and Transient Transfections

CV-1 cells were maintained in DMEM supplemented with 10%. Fetal Bovine Serum. Transient transfections were performed using DOTAP transfection reagent (Boehringer-Mannheim). Transfections using β-galactosidase as the reporter were assayed either by Galactolight luminescent assay (Tropix, Bedford, Mass.) or by standard liquid ONPG assay (Sigma, St. Louis, Mo.). The values were normalized by co-transfection of CMX-luciferase. Transfections using luciferase as the reporter were assayed by standard techniques using luciferin and ATP. These values were normalized by co-transfection of CMX-β-galactosidase. Hormone treated cells were treated with ethanol, 50 μM Juvenile Hormone III (Sigma), 1 μM muristerone A (Zambon, Bresso, IT), or 1 μM dexamethasone (Sigma) unless otherwise noted.

To maximize the sensitivity of the invention ecdysone inducible system, modifications of the ecdysone receptor were made. The N-terminal transactivation domain of the ecdysone receptor was replaced by the corresponding domain of the glucocorticoid receptor (GR), resulting in the modified ecdysone receptor GEcR (See FIG. 1D). CV-1 cells were transfected with the plasmid CMX-GEcR encoding the modified ecdysone receptor as discussed above. After transfection, cells were either treated with ethanol or 1 μM muristerone A. This hybrid modified ecdysone receptor boosted muristerone responsiveness from 3- to 11-fold in a transient transfection assay (FIG. 1A). Replacement of the natural heterodimeric partner for the ecdysone receptor, USP, by its mammalian homologue, the retinoid X receptor (RXR), produced a more potent ligand dependent heterodimer, providing a 34 fold induction (FIG. 1A).

Figure 1B:
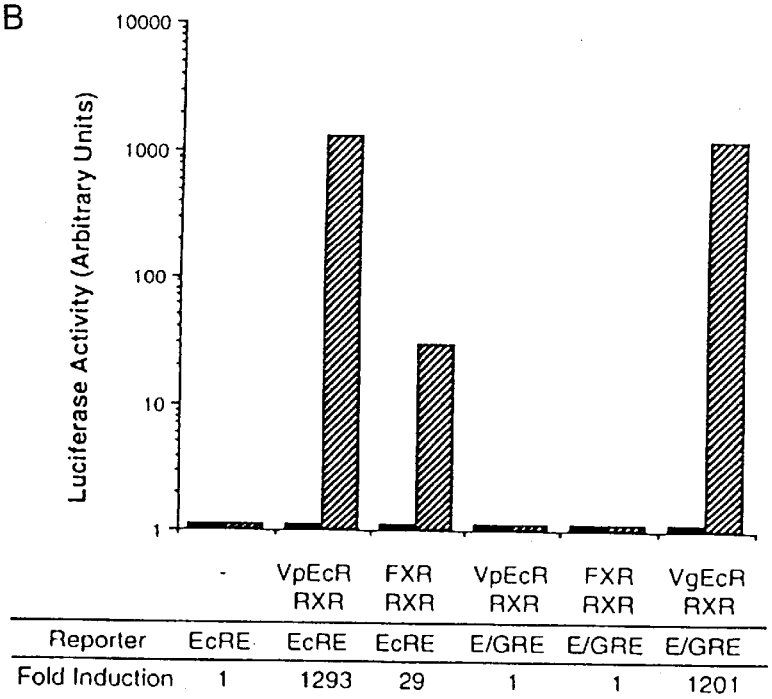
Figure 1C:
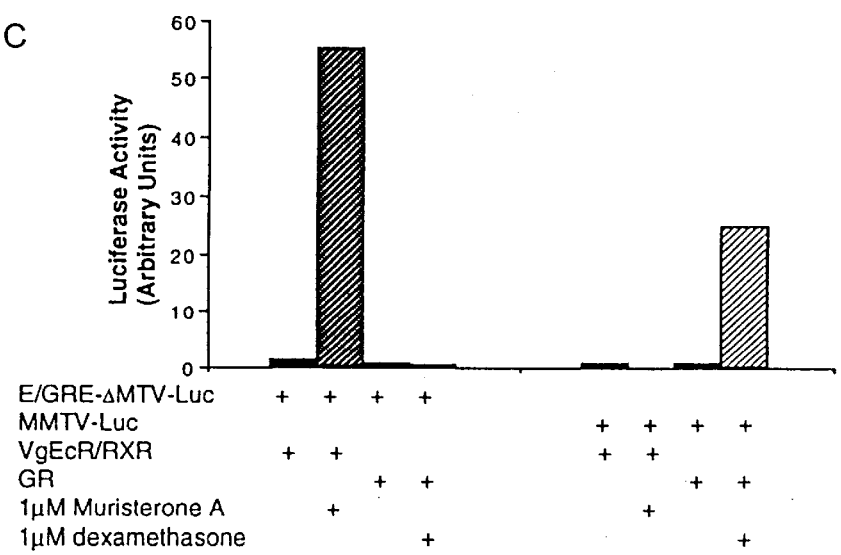
Figure 1D:
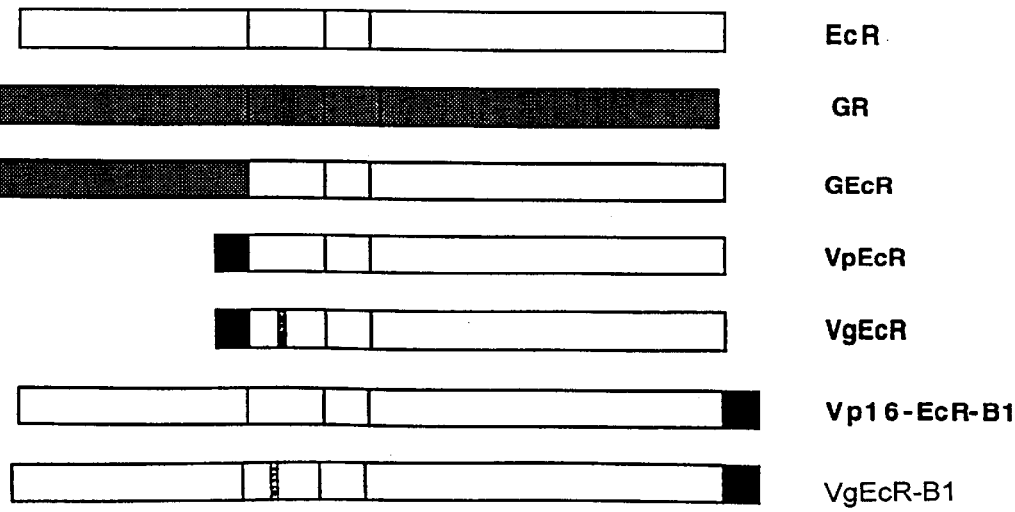

A more potent heterodimer, however, was obained by combining RXR and VpEcR, an N-terminal truncation of the ecdysone receptor attached to the VP16 activation domain, resulting in a 212 fold induction (FIGS. 1A and 1D). Different from most nuclear receptor/VP16 fusion proteins which exhibit high constitutive activity, VpEcR generates ligand dependent superinduction while maintaining a very low basal activity (Underhill et al., *Mol. Encod.* 8:274–285 (1994) and Perlmann et al., *Genes & Devel.* 7:1411–1422 (1993)).

In addition, the reporter vector was also modified by inserting consensus binding sites for the ubiquitous transcription factor Sp1 between the minimal promoter and the ecdysone response elements (Kamine et al., *Proc. Natl. Acad. Sci.* 88:8510–8514 (1991) and Strahle te al., *EMBO* 7:3389–3395 (1988)). The addition of Sp1 sites to the ecdysone responsive promoter increases the absolute activity 5-fold (FIG. 1A).

EXAMPLE 2

Construction of a Novel Ecdysone Response Element

Although no mammalian transcription factors have been shown to have a natural enhancer element like the ecdysone response element, which is composed of two inverted half-sites of the sequence AGGTCA spaced by one nucleotide, it is difficult to preclude such a possibility. The recently cloned farnesoid X receptor (FXR) can very weakly activate certain synthetic promoters containing an ecdysone response element in response to extremely high concentrations of farnesoids (Forman et al., *Cell* 81:687–693 (1995)).

In FXR containing cells and in transgenic mice, activation of gene expression by endogenous receptors would create undesirable background levels of reporter protein. To circumvent this potential problem, the DNA binding specificity of VpEcR was altered to mimic that of GR, which binds as a homodimer to an inverted repeat of the sequence AGAACA, spaced by three nucleotides. This altered binding specificity was achieved by mutating three amino acid residues of VpEcR in the P-box of the DNA binding domain, a region previously shown to be essential for DNA sequence recognition (Umesono and Evans, *Cell* 57:1139–1146 (1989)). This new hybrid modified ecdysone receptor is referred herein as VgEcR and is responsive to a new hybrid respone element referred to herein as the E/GRE (SEQ ID NO:12), which contains two different half-site motifs, RGBNNM and RGNNCA, spaced by one nucleotide (FIG. 1B). This new response element is a hybrid between the glucocorticoid response element (GRE) and that of type II nuclear receptors like RXR, EcR, retinoic acid receptor (RAR), thyroid hormone receptor (T3R), etc. Although FXR can activate a promoter containing the wild type ecdysone response element, it cannot activate one containing the E/GRE (FIG. 1B; note log scale). The E/GRE reporter is not activated by GR nor does VgEcR activate a dexamethasone responsive promoter (FIG. 1C).

EXAMPLE 3

Assay for Ecdysone Responsiveness in Stable Cell Lines

Stable cell lines were generated containing the modified ecdysone receptor VpEcR, a heterodimeric partner (RXR), and an ecdysone inducible reporter (FIG. 2). 293 cells were transfected with the following linearized plasmids, pRC-ESHβ, EcREx5-ΔMTV-Luc, CMX-VpEcR, and CMX-hRXRa. The following day, the cells were split 1:10 and were allowed to recover one day prior to selection with 1 mg/ml G418 (GIBCO). After 14 days of selection, 14 individual clones were isolated and grown separately in the presence of 0.5 mg/ml G418. Of 14 G418 resistant clones, 10 demonstrated differing degrees of muristerone responsiveness.

One of these cell lines, N13, was grown in the presence or absence of 1 μM muristerone for 20 hours. Cell lysates were then assayed for β-galactosidase and luciferase activities as described in Example 1. X-gal staining was performed on the stable cell lines. Cells were fixed briefly with 10% formaldehyde in PBS and then stained with X-Gal (Molecular Probes, Eugene, Oreg.) for 2 to 6 hours. After 24 hours of treatment with 1 μM muristerone, 100% of the cells turned dark blue after 3 hours of staining. Thus, mammalian cells containing the modified ecdysone receptor VpEcR, a heterodimeric partner (RXR), and a reporter gene construct regulated by a modified ecdysone response element, function to efficiently express an exogenous gene in response to a ligand, e.g., ecdysone.

Figure 3A:
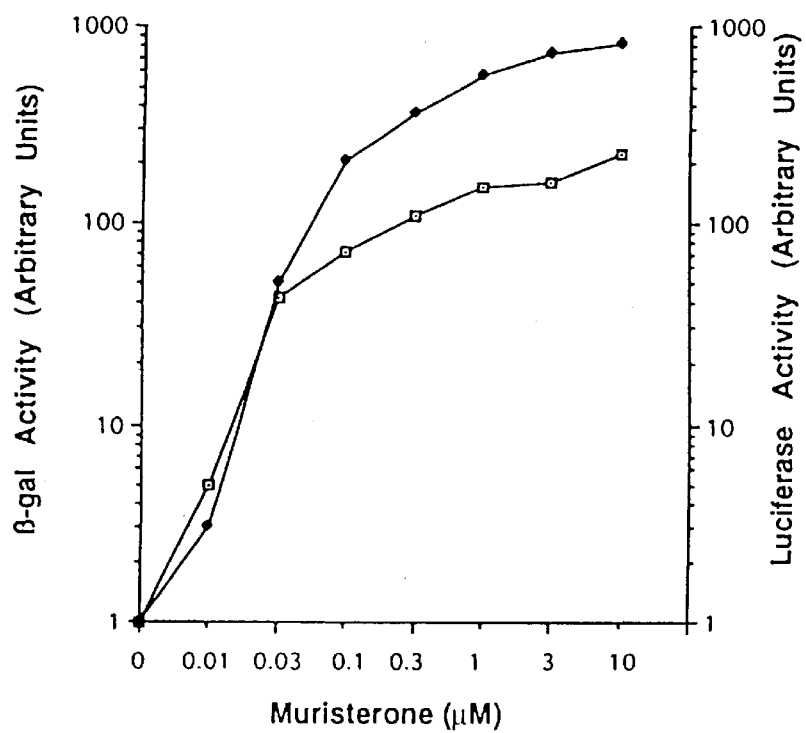
FIG. 3A shows a dose-dependent activation of N13 cells with muristerone. N13 cells were grown with varying concentrations of muristerone for 36 hours and then assayed for $\beta$-galactosidase activity (open squares) by standard ONPG assay or for luciferase activity (closed circles).

A dose-response assay was conducted by growing N13 cells with varying concentrations of muristerone for 36 hours and then assaying for β-galactosidase activity (using the well-known ONPG assay), or the cells were assayed for luciferase activity. Dose response curves of stably integrated β-galactosidase and luciferase reporters in N13 cells revealed that inducibility approaching 3 orders of magnitude can be achieved at a final concentration 10 μM muristerone (FIG. 3A). One-hundred fold induction was achieved by muristerone concentrations as low as 100 nM (FIG. 3A).

Figure 3B:
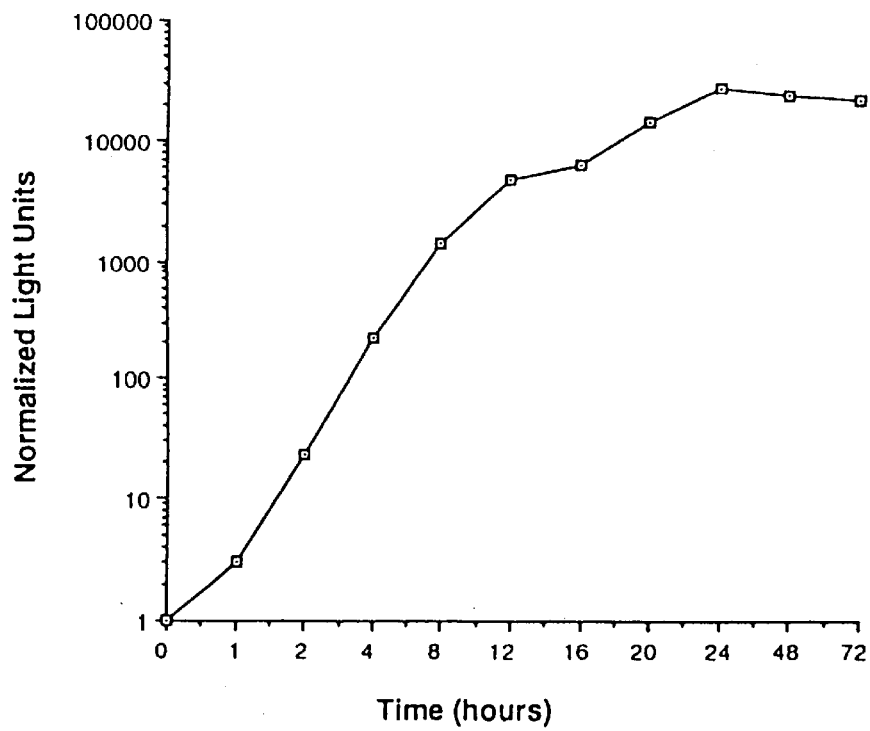
FIG. 3B shows the time-course of luciferase activity of N13 cells treated with hormone. N13 cells were grown in separate wells in the presence of 1 $\mu$M muristerone, harvested at varying times, and assayed for luciferase activity as described in Example 3.

Finally, the kinetics of muristerone mediated induction was measured. N13 cells were grown in separate wells in the presence of 1 μM muristerone, harvested at varying times, and assayed for luciferase activity. Inductions of 100-fold in 3 hrs., 1000 fold in 8 hrs., and maximal effects of 20,000 fold after 20 hours of treatment were observed (FIG. 3B). Similar results were observed in stable lines containing CMX-VgEcR and the E/GRE reporters.

EXAMPLE 4

Bioavailability and Activity of Muristerone

In order to use muristerone as a potential hormone in mice, its toxicity and bioavailability was examined. For toxicity studies, adult mice were injected intraperitonealy with 20 mg of muristerone A suspended in sesame oil. The mice were then observed for approximately two months. For teratogenic studies, pregnant mice were injected with 20 mg of muristerone A suspended in sesame oil and both the mother and pups were observed for three months. The results indicate that muristerone maintains its activity when injected into mice, and that it is neither toxic, teratogenic, nor inactivated by serum binding proteins. In addition to the inert qualities of muristerone (an ecdysone), overexpression of VpEcR and RXR appears not to be toxic.

For muristerone bioavailability studies, adult mice were injected intraperitoneally with sesame oil with or without 10 μmg of muristerone, and were subsequently sacrificed for serum collection. After twelve hours, blood was drawn from the mice, and the serum was isolated by brief centrifugation of the whole blood. In order to conduct transfection assays to test for muristerone activity, serum from sesame oil injected mice was divided, and half was supplemented with muristerone to a final concentration of 10 μM. The three batches of mouse serum were diluted 1:10 in DMEM and placed onto CV-1 cells transfected with CMX-GEcR, CMX-hRXRa, and EcREx5-DMTV-Luc.

Figure 4:
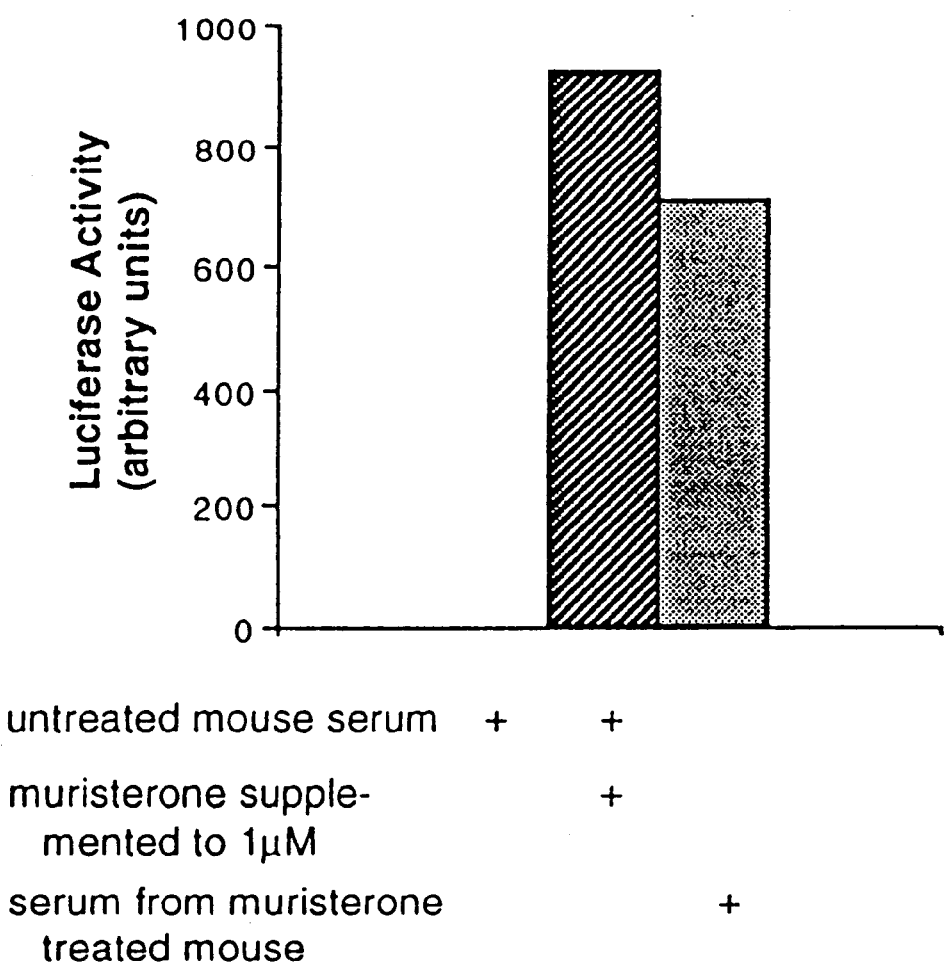
FIG. 4 shows muristerone activity in mice as described in Example 4.

The results are shown in FIG. 4 and indicate that serum from muristerone treated mice yielded a luciferase activity comparable to that seen from untreated mouse serum supplemented with 1 μM muristerone. The results indicate that single-site injected material should be widely circulated, and that there is little or no blunting of activity due to association with serum proteins.

EXAMPLE 5

Muristerone Dependent Gene Expression in Transgenic Mice

To produce transgenic mice, the following DNA constructs were prepared and subsequently injected into fertilized eggs: CD3-VpEcR, CD3-RXR, ESHβ (Lee et al., *J. Exp. Med.* 175:1013–1025 (1992)). Two separate lines of transgenic mice were generated harboring either an ecdysone inducible reporter, ESHβ, or a T-cell specific expression construct of VpEcR and RXR, respectively. The former are referred to as reporter mice, the latter are referred to as receptor mice, and double transgenic mice are referred to as receptor/reporter mice. Constructs CD3-VpEcR and CD3-RXR were mixed and coinjected, while ESHB was injected alone. Primary genotyping was performed by Southern blot analysis and the transmission of transgenic mice was monitored by dot blot analysis. Receptor mice were analyzed for VpEcR and RXR expression by Northern blot analysis of RNA collected from these mice. For Northern blot analysis, 15 μg of total RNA obtained from the thymus, and various tissues as a control, was run on a denaturing gel and blotted onto a nitrocellulose membrane. The blot was probed with a radiolabeled β-gal-specific probe and exposed on film for 2 days. These receptor mice were healthy, fertile, and appeared normal by visual inspection. In addition, the transgene was transferred to the offspring as expected by Mendelian genetics. This data suggests that overexpression of VpEcR and RXR in T-cells is not toxic.

Receptor expressing mice were bred with reporter mice (containing ESHβ) to produce double transgenic receptor/reporter mice. Adult receptor/reporter transgenic mice (genotype=CD3-VpEcR; CD3-RXR; and ESHβ) were injected intraperitonealy with sesame oil with or without 10 mg of muristerone. Subsequently, a Northern blot analysis was performed on the double transgenic lines using RNA isolated 48 hours after treatment from various tissues including the thymus, brain and liver, to test for the specific induction of an ecdysone inducible promoter. The probe used was specific to the activity of the ecdysone inducible promoter. The autoradiograph was exposed for 36 hrs. The results of the Northern analysis indicate that muristerone treatment of the transgenic mouse containing a T-cell specific expression construct of VpEcR and RXR, and the ecdysone inducible reporter ESHB, caused a significant induction from an ecdysone inducible promoter in the thymus, while low basal activity is observed in its absence.

EXAMPLE 6

Assay for Ponasterone Responsiveness

Figure 5:
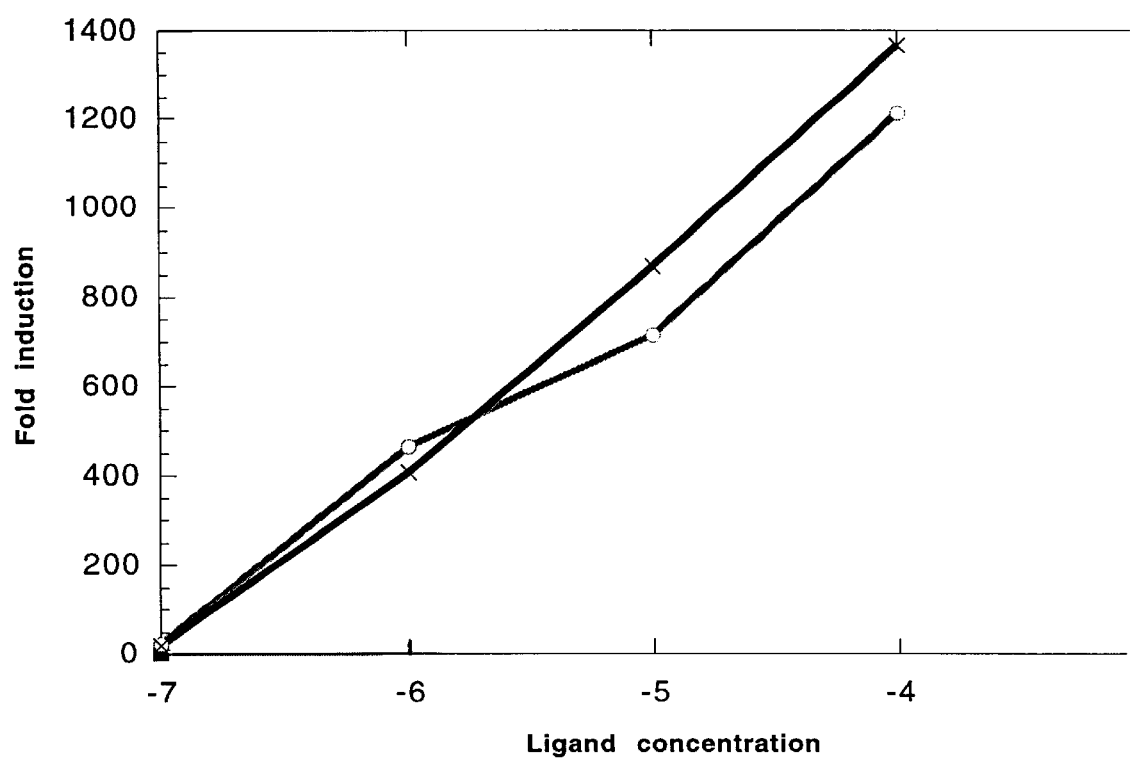
FIG. 5 compares the dose-dependent activation of N13 cells with muristerone (X) and ponasterone A (open circles).

A dose-response assay was conducted as described in Example 3, by growing N13 cells with varying concentrations of muristerone or ponasterone A for 36 hours and then assaying for β-galactosidase activity (using the well-known ONPG assay), or the cells were assayed for luciferase activity. Dose response curves of stably integrated β-galactosidase and luciferase reporters in N13 cells revealed that inducibility exceeding 3 orders of magnitude can be achieved with both ligands at final concentrations of about $10^{-4}$ (see FIG. 5).

While the invention has been described in detail with reference to certain preferred embodiments thereof, it will be understood that modifications and variations are within the spirit and scope of that which is described and claimed.

That which is claimed is:

1. A method for modulating the expression of an exogenous gene in an isolated cell containing:
   (i) a modified ecdysone receptor which, in the presence of a ligand therefor, and optionally in the further presence of a silent partner therefor, binds to a response element, wherein said modified ecdysone receptor comprises:
      (a) a ligand binding domain that binds to an ecdysteroid,
      (b) a DNA-binding domain obtained from a DNA-binding protein, which binds to said response element; and
      (c) an activation domain of a transcription factor, wherein at least one of said DNA-binding domain or said activation domain is not obtained from a native ecdysone receptor, with the proviso that when said activation domain is derived from a glucocorticoid receptor, said DNA-binding domain is not derived from a glucocorticoid receptor or a E. coli LexA protein; and
   (ii) a DNA construct comprising said exogenous gene under the control of said response element, wherein said response element:
      (a) is a modified response element which comprises, in any order, a first half-site and a second half-site separated by a spacer of 0–5 nucleotides;
      wherein said first half-site has the sequence:

—RGBNNM—, wherein
      each R is independently selected from A or G;
      each B is independently selected from G, C, or T;
      each N is independently selected from A, T, C, or G; and
      each M is independently selected from A or C;
      with the proviso that at least 4 nucleotides of each —RGBNNM—group of nucleotides are identical with the nucleotides at comparable positions of the sequence —AGGTCA—;
      and wherein said second half-site is obtained from a glucocorticoid receptor subfamily response element,
      (b) binds to said modified ecdysone receptor, and
      (c) does not bind to farnesoid X receptor (FXR);
   said method comprising providing to the cell an effective amount of one or more ligands for said modified ecdysone receptor; wherein said one or more ligands are not normally present in the cell; and wherein said one or more ligands are not toxic to said cell.

2. A method according to claim 1 wherein said modified ecdysone receptor is further characterized as having substantially no constitutive activity in mammalian cells.

3. A method according to claim 1 wherein the DNA-binding domain of said modified ecdysone receptor is derived from a nuclear receptor.

4. A method according to claim 1 wherein said activation domain is obtained from a nuclear receptor.

5. A method according to claim 1 wherein said activation domain is a glucocorticoid receptor activation domain, a VP16 activation domain or a GAL4 activation domain.

6. A method according to claim 5 wherein said modified ecdysone receptor is VpEcR, VgEcR or GecR.

7. A method according to claim 6 wherein said modified ecdysone receptor is VgEcR having the amino acid sequence set forth in SEQ ID NO:5.

8. A method according to claim 1 wherein said modified ecdysone receptor is present primarily in the form of a homodimer.

9. A method according to claim 1, wherein said silent partner is RXR.

10. A method according to claim 9 wherein said RXR is exogenous to said cell.

11. A method according to claim 1 wherein said ligand is a naturally occurring ecdysone, an ecdysone-analog or an ecdysone mimic.

12. A method according to claim 11 wherein said naturally occurring ecdysone is α-ecdysone or β-ecdysone.

13. A method according to claim 11 wherein said ecdysone analog is ponasterone A, ponasterone B, ponasterone C, 26-iodoponasterone A, muristerone A, inokosterone or 26-mesylinokosterone.

14. A method according to claim 11 wherein said ecdysone mimic is 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkyl-N'-aroyl hydrazine.

15. A method according to claim 1 wherein said exogenous gene is a wild type gene and/or gene of interest.

16. A method according to claim 15 wherein said wild type gene encodes products:
   the substantial absence of which leads to the occurrence of a non-normal state in said cell; or
   a substantial excess of which leads to the occurrence of a non-normal state in said cell.

17. A method according to claim 15 wherein said gene of interest encodes products:
   which are toxic to the cells in which they are expressed; or
   which impart a beneficial property to cells in which they are expressed.

18. A method of inducing the expression of an exogenous gene in an isolated cell containing:
   (i) DNA encoding a modified ecdysone receptor under the control of an inducible promoter, wherein said modified ecdysone receptor, in the presence of a ligand therefor, and optionally in the further presence of a silent partner therefor, binds to a response element, and wherein said modified ecdysone receptor comprises:
      (a) a ligand binding domain that binds to an ecdysteroid,
      (b) a DNA-binding domain obtained from a DNA-binding protein, which binds to said response element; and
      (a) an activation domain of a transcription factor, wherein at least one of said DNA-binding domain or said activation domain is not obtained from a native ecdysone receptor, with the proviso that when said activation domain is derived from a glucocorticoid receptor, said DNA-binding domain is not derived from a glucocorticoid receptor or an E. coli LexA protein;
   (ii) a DNA construct comprising said exogenous gene under the control of said response element, wherein said response elements;
      (a) is a modified response element which comprises, in any order, a first half-site and a second half-site separated by a spacer of 0–5 nucleotides;
      wherein said first half-site has the sequence:

—RGBNNM—, wherein
      each R is independently selected from A or G;
      each B is independently selected from G, C, or T;

each N Is independently selected from A, T, C, or G; and each M is independently selected from A or C;

with the proviso that at least 4 nucleotides of each —RGBNNM—group of nucleotides are identical with the nucleotides at comparable positions of the sequence —AGGTCA—;

and wherein said second half-site is obtained from a glucocorticoid receptor subfamily response element, (b) binds to said modified ecdysone receptor, and (c) does not bind to farnesoid X receptor (FXR); and (iii) one or more ligands for said modified ecdysone receptor;

said method comprising subjecting said cell to conditions suitable to induce expression of said modified ecdysone receptor.

19. A method of inducing expression of an exogenous gene in an isolated cell containing a DNA construct containing said exogenous gene under the control of a response element, wherein said response element:

(a) is a modified response element which comprises, in any order, a first half-site and a second half-site separated by a spacer of 0–5 nucleotides;

wherein said first half-site has the sequence;

—RGBNNM—, wherein each R is independently selected from A or G;

each B is independently selected from G, C, or T;

each N is independently selected from A, T, C, or G; and each M is independently selected front A or C;

with thy proviso that at least 4 nucleotides of each —RGBNNM—group of nucleotides are identical with the nucleotides at comparable position of the sequence —AGGTCA—;

and wherein said second half-site is obtained from a glucocorticoid receptor subfamily response element, (b) binds to said modified ecdysone receptor, and (c) does not bind to farnesoid X receptor (FXR), said method comprising introducing into said cell;

a modified ecdysone receptor, wherein said modified ecdysone receptor comprises: (a) a ligand binding domain that binds to an ecdysteroid, (b) a DNA-binding domain obtained from a DNA-binding protein, which binds to said response element; and (c) an activation domain of a transcription factor, wherein at least one of said DNA-binding domain or said activation domain is not obtained from a native ecdysone receptor, with the proviso that when said activation domain is derived from a glucocorticoid receptor, said DNA-binding domain is not derived from a glucocorticoid receptor or an E. coli LexA protein; and one or more ligands for said modified ecdysone receptor, wherein said receptor, in combination with a ligand therefor, and optionally in the further presence of a silent partner therefor, binds to said response element, activating transcription therefrom.

20. A method for the expression of a recombinant product detrimental to isolated host cells, said method comprising: transforming suitable isolated host cells with:

(i) DNA encoding a modified ecdysone receptor, wherein said modified ecdysone receptor comprises:

(a) a ligand binding domain that binds to an ecdysteroid, (b) a DNA-binding domain obtained from a DNA-binding protein; and (c) an activation domain of a transcription factor, wherein at least one of said DNA-binding domain or said activation domain is not obtained from a native ecdysone receptor, with the proviso that when said activation domain is derived from a glucocorticoid receptor, said DNA-binding domain is not derived from a glucocorticoid receptor or an E. coli LexA protein; and (ii) a DNA construct encoding said recombinant product under the control of a response element, wherein said response element;

(a) is a modified response element which comprises, in any order, a first half-site and a second half-site separated by a spacer of 0–5 nucleotides;

wherein maid first half-site has the sequence;

—RGBNNM—, wherein each R is independently selected from A or G;

each B is independently selected from G, C, or G;

each N is independently selected from A, T, C, or G; and each M is independently selected from A or C;

with the proviso that at least 4 nucleotides of each —RGBNNM—group of nucleotides are identical with the nucleotides at comparable positions of the sequence —AGGTCA—;

and wherein said second half-site is obtained from a glucocorticoid receptor subfamily response element (b) binds to said modified ecdysone receptor, and (c) does not bind to farnesoid X receptor (FXR); growing said host cells in suitable media; and inducing expression of said recombinant product by introducing into said host cells one or more ligands for said modified ecdysone receptor, and optionally a silent partner for said modified ecdysone receptor.

21. A method according to claim 1, wherein said first half-site is obtained from an ecdysone response element and said second half-site is obtained from a glucocorticoid response element, a mineralocorticoid response element, a progesterone response element or an androgen response element.

22. A method according to claim 21, wherein said second half-site is obtained from a glucocorticoid response element.

23. A method according to claim 1, wherein said silent partner is present.

24. A method according to claim 23 wherein said silent partner is ultraspiracle.

25. A method according to claim 1 wherein said modified ecdysone receptor does not bind to endogenous response elements.

* * * * *

UNITED STATES PATENT AND TRADEMARK OFFICE
CERTIFICATE OF CORRECTION

PATENT NO.    : 6,723,531 B2
DATED         : April 20, 2004
INVENTOR(S)   : Ronald M. Evans, David No and Enrique Saez It is certified that error appears in the above-identified patent and that said Letters Patent is hereby corrected as shown below:

<u>Column 65,</u>
Line 11, change "clem" to -- elem --
Line 19, after "or," change "a" to -- an --

<u>Column 66,</u>
Line 58, change "elements;" to -- element: --

<u>Column 67,</u>
Line 33, change "front" to -- from --
Line 34, change "thy" to -- the --
Line 36, change "position" to -- positions --

<u>Column 68,</u>
Line 18, change the semicolon after "element" to a colon
Line 22, change the semicolon after "sequence" to a colon
Line 28, change "or G;" to -- or T; --

Signed and Sealed this

Ninth Day of November, 2004

JON W. DUDAS
*Director of the United States Patent and Trademark Office*